US008030032B2

(12) United States Patent
Adelson et al.

(10) Patent No.: US 8,030,032 B2
(45) Date of Patent: Oct. 4, 2011

(54) METHODS AND COMPOSITIONS RELATED THERETO FOR DETECTING AND IDENTIFYING DISTINCT SPECIES OF NUCLEIC ACIDS FROM CAUSATIVE AGENTS

(75) Inventors: Martin E. Adelson, Hillsborough, NJ (US); Melanie Feola, Cherry Hill, NJ (US); Jason Trama, Burlington, NJ (US); Eli Mordechai, Robbinsville, NJ (US)

(73) Assignee: Medical Diagnostic Lab, LLC, Hamilton, NJ (US)

( * ) Notice: Subject to any disclaimer, the term of this patent is extended or adjusted under 35 U.S.C. 154(b) by 393 days.

(21) Appl. No.: 11/246,976

(22) Filed: Oct. 7, 2005

(65) Prior Publication Data

US 2006/0088865 A1  Apr. 27, 2006

Related U.S. Application Data

(60) Provisional application No. 60/616,723, filed on Oct. 7, 2004.

(51) Int. Cl.
C12P 19/34 (2006.01)
(52) U.S. Cl. ....................................... 435/91.2
(58) Field of Classification Search .................. 435/91.2
See application file for complete search history.

(56) References Cited

U.S. PATENT DOCUMENTS

| 5,244,792 A | 9/1993 | Burke et al. |
| 5,648,079 A * | 7/1997 | Burke et al. ............... 424/186.1 |
| 2002/0164586 A1 | 11/2002 | Smith et al. |
| 2004/0175753 A1 | 9/2004 | Chen et al. |

OTHER PUBLICATIONS

Oliver et al., "Use of Single Nucleotide Polymorphisms (SNP) and Real-Time Polymerase Chain Reaction for Bone Marrow Engraftment Analysis," J.Mol.Diag., 2000, vol. 2, No. 4, pp. 202-208.*
Lee et al., "Allelic discrimination by nick-translation PCR with fluorogenic probes," Nucleic Acids Research, 1993, vol. 21, No. 16, pp. 3761-3766.*
Josefsson et al., "Detection and Quantification of Human Papillomavirus by Using the Fluorescent 5' Exonuclease Assay," J. Clinical. Micro., 1999, vol. 37, No. 3, pp. 490-496.*
Ryncarz et al., "Development of a High-Throughput Quantitative Assay for Detecting Herpes Simplex Virus DNA in Clinical Samples," J.Clinical Micro., 1999, vol. 37, No. 6, pp. 1941-1947.*
Peter et al., "Review of 3200 serially received CSF samples submitted for type-specific HSV detection by PCR in the reference laboratory setting," Mol.Cell.Probes, 2001, vol. 15, pp. 177-182.*
Buck et al., "Design Strategies and Performance of Custom DNA Sequencing Primers," Biotechniques, Sep. 1999, vol. 27, No. 3, pp. 528-536.*
Burrows et al., "Detection and subtyping of Herpes Simplex virus in clinical samples by LightCycler PCR, enzyme immunoassay and cell culture," BMC Microbiology, Jun. 2002, vol. 2, No. 12, pp. 1-7.*
Filen et al , Sexually Transmitted Diseases, vol. 31, No. 6, pp. 331-336, Jun. 2004.*
Schalasta et al, Infection, vol. 28, pp. 85-91, 2000.*
Hardy et al, The Journal of Infectious Diseases, vol. 162, No. 5, pp. 1031-1035, Nov. 1990.*
National Center for Biotechnology Information (NCBI) accession No. X14112 (Human herpesvirus 1 complete genome).
National Center for Biotechnology Information (NCBI) accession No. Z86099 (Herpes simplex virus type 2 (strain HG52), complete genome).
Adelson et al. (2004) Development of a real-time PCR assay for the simultaneous detection of herpes simplex virus types 1 and 2 with confirmation by pyrosequenceing technology. Presented by Dr. Martin E. Adelson at the 104th General Meeting of the American Society of Microbiology in New Orleans, Lousiana on May 26, 2004 as Poster C-273.
Adelson et al. (2005) Simultaneous detection of herpes simplex virus types 1 and 2 by real-time PCR and pyrosequencing. Journal of Clinical Virology 33:25-34.
Cusini et al. (2001) The importance of diagnosing genital herpes. Journal of Antimicrobial Chemotherapy 47, Topic T1, 9-16.
Xu et al. (2002) Seroprevalence and coinfection with herpes simplex virus type 1 and type 2 in the United States, 1988-1994. The Journal of Infectious Diseases 185:1019-1024.
Weidmann et al. (2003) Rapid detection of herpes simplex virus and varicella-zoster virus infections by real-time PCR. Journal of Clinical Microbiology 41(4):1565-1568.
Wald et al. (2003) Polymerase chain reaction for detection of herpes simplex virus (HSV) DNA on mucosal surfaces: comparison with HSV isolation in cell culture. The Journal of Infectious Diseases 188:1345-1351.

(Continued)

*Primary Examiner* — Gary Benzion
*Assistant Examiner* — Cynthia Wilder
(74) *Attorney, Agent, or Firm* — Siu K. Lo

(57) ABSTRACT

Methods are described herein for detecting and identifying distinct species of nucleic acids, in a single container, for example, from a certain genus of infectious agents or otherwise causative agents comprising, for example, providing a forward PCR primer common to a homologous gene region between the distinct species, and providing a reverse PCR primer common to a homologous gene region between the distinct species, to thereby define a PCR target region amongst the species, and providing a first oligonucleotide probe specific to a nucleic acid sequence within the target region that is characteristic of a first species, providing a second oligonucleotide probe specific to a nucleic acid sequence within the target region that is characteristic of a second species, wherein the first and second oligonucleotide probes are each detectably labeled with distinctly different detectable labels, conducting a PCR reaction in the container by means of the primers to amplify the target region amongst the species, and detecting the distinct labels, thereby identifying distinct species of nucleic acids corresponding to distinct species of infectious agents. Methods are preferred, for example, wherein the infectious agent is a member of the Herpesviridae family.

10 Claims, 4 Drawing Sheets

OTHER PUBLICATIONS van Doornum et al. (2003) Diagnosing herpesvirus infections by real-time amplification and rapid culture. Journal of Clinical Microbiology 41(2):576-580.

Altschul et al. (1997) Gapped BLAST and PSI-BLAST: a new generation of protein database search programs. Nucleic Acids Research 25(17)3389-3402.

Cone et al. (1994) Frequent detection of genital herpes simplex virus DNA by polymerase chain reaction among pregnant women. The Journal of the American Medical Association 272(10):792-796.

Cone et al. (1991) Extended duration of herpes simplex virus DNA in genital lesions detected by the polymerase chain reaction. The Journal of Infectious Diseases 164(4):757-760.

Lucotte et al. (1995) Detection and genotyping of herpes simplex virus types 1 and 2 by polymerase chain reaction. Molecular and Cellular Probes 9(5):287-90.

Nicoll et al. (2001) Detection of herpes viruses in clinical samples using real-time PCR. Journal of Virological Methods 96(1):25-31.

Schmutzhard et al. (2004) Detection of herpes simplex virus type 1, herpes simplex virus type 2 and varicella-zoster virus in skin lesions. Comparison of real-time PCR, nested PCR and virus isolation. Journal of Clinical Virology 29(2):120-126.

Gharizadeh et al. (2002) Long-read pyrosequencing using pure 2'-deoxyadenosine-5'-O'-(1-thiotrlphosphate) Sp-isomer. Analytical Biochemistry 301(1):82-90.

Ronaghi et al. (1998) A sequencing method based upon real-time pyrophosphate. Science 281(5375):363, 365.

Poljak et al. (1998) Simple one-tube reverse transcription-polymerase chain reaction protocol containing anticontamination procedure for detection of GB virus C/hepatitus G virus RNA. Journal of Virological Methods 71(1):1-6.

Newcombe (1998) Two-sided confidence intervals for the single proportion: comparison of seven methods. Statistics in Medicine 17(8):857-872.

Stocher et al. (2003) Parallel detection of five human herpes virus DNAs by a set of real-time polymerase chain reactions in a single run. Journal of Clinical Virology 26(1):85-93.

* cited by examiner

FIG.1

```
ATCACAGGTCGTCCTCGTCGGCGTCACCGTCTTTGTTGGGAACTTGGGTGTAGTTGGTGTTGCGGCGCTTGCGCA
TGACCATGTCGGTGACCTTGGCGCTGAGCAGCGCGCTCGTGCCCTTCTTCTTGGCCTTGTGTTCCGTGCGCTCCA
TGGCAGACACCAGGGCCATGTACCGTATCATCTCCCGGGCCTCGGCTAGCTTGGCCTCGTCAAAGTCGCCGCCCT
CCTCGCCCTCCCCGGACGCGTCCGGGTTGGTGGGGTTCTTGAGCTCCTTGGTGGTTAGCGGGTACAGGGCCTTCA
TGGGGTTGCTCTGCAGCCGCATGACGTAGCGAAAGGCGAAGAAGGCCGCCGCCAGGCCGGCCAGGACCAACAGAC
CCACGGCCAGCGCCCCAAAGGGGTTGGACATGAAGGAGGACACGCCCGACACGGCCGATACCACGCCGCCCACGA
TGCCCATCACCACCTTGCCGACCGCGCGCCCCAGGTCGCCCATCCCCTCGAAGAACGCGCCCAGGCCCGCAAACA
TGGCGGCGTTGGCGTCGGCGTGGATGACCGTGTCGATGTCGGCGAAGCGCAGGTCGTGCAGCTGGTTGCGGCGCT
GGACCTCCGTGTAGTCCAGCAGGCCGCTGTCCTTGATCTCGTGGCGGGTGTACACCTCCAGGGGGACAAACTCGT
GATCCTCCAGCATGGTGATGTTGAGGTCGATGAAGGTGCTGACGGTGGTGATGTCGGCGCGGCTCAGCTGGTGGG
AGTACGCGTACTCCTCGAAGTACACGTAGCCCCCACCGAAGGTGAAGTAGCGCCGGTGTCCCACGGTGCACGGCT
CGATCGCATCGCGCGTCAGCCGCAGCTCGTTGTTCTCCCCAGCTGCCCCTCGACCAACGGGCCCTGGTCTTCGT
ACCGAAAGCTGACCAGGGGCGGCTGTAGCAGGCCCCGGGCCGCGAGCTGATGCGCATCGAGTTTTGGACGATCA
CGTTGTCCGCGGCGACCGGCACGCACGTGGAGACGGCCATCACGTCGCCGAGCATCCGCGCGCTCACCCGCCGGC
CCACGGTGGCCGAGGCGATGGCGTTGGGGTTCAGCTTGCGGGCCTCGTTCCACAGGGTCAGCTCGTGATTCTGCA
GCTCGCACCACGCGATGGCAACGCGGCCCAACATATCGTTGACATGGCGCTGTATGTGGTTGTACGTAAACTGCA
GCCTGGCGAACTCGATGGAGGAGGTGGTCTTGATGCGCTCCACGGACGCGTTGGCGCTGGCCCCGGGCGGCGGGG
GCGTGGGGTTTGGGGGCTTGCGGCTCTGCTCGCGGAGGTGTTCCCGCACGTACAGCTCCGCGAGCGTGTTGCTGA
GAAGGGGCTGGTACGCGATCAGAAAGCCCCCATTGGCCAGGTAGTACTGCGGCTGGCCCACCTTGATGTGCGTCG
CGTTGTACCTGCGGGCGAAGATGCGGTCCATGGCGTCGCGGGCGTCCTTGCCGATGCAGTCCCCCAGGTCCACGC
GCGAGAGCGGGTACTCGGTCAGGTTGGTGGTGAAGGTGGTGGATATGGCGTCGGAAGAGAATCGGAAGGAGCCGC
CGTACTCGGAGCGCAGCATCTCGTCCACCTCCTGCCACTTGGTCATGGTGCAGACCGACGGGCGCTTTGGCACCC
AGTCCCAGGCCACGGTGAACTTGGGGGTCGTGAGCAGGTTCCGGGTGGTCGGCGCCGTGGCCCGGGCCTTGGTGG
TGAGGTCGCGCGCGTAGAAGCCGTCGACCTGCTTGAAGCGGTCGGCGGCGTAGCTGGTGTGTTCGGTGTGCGACC
CCTCCCGGTAGCCGTAAAACGGGGACATGTACACAAAGTCGCCAGTCGCCAACACAAACTCGTCGTACGGGTACA
CCGAGCGCGCGTCCACCTCCTCGACGATGCAGTTTACCGTCGTCCCGTACCGGTGGAACGCCTCCACCCGCGAGG
GGTTGTACTTGAGGTCGGTGGTGTGCCAGCCCCGGCTCGTGCGGGTCGCGGCGTTGGCCGGTTTCAGCTCCATGT
CGGTCTCGTGGTCGTCCCGGTGAAACGCGGTGGTCTCCAGGTTGTTGCGCACGTACTTGGCCGTGGACCGACAGA
CCCCCTTGGCGTTGATCTTGTCGATCACCTCCTCGAAGGGGACGGGGCGCGGTCCTCAAAGATCCCCATAAACT
GGGAGTAGCGGTGGCCGAACCACACCTGCGAAACGGTGACGTCTTTGTAGTACATGGTGGCCTTGAACTTGTACG
GGGCGATGTTCTCCTTGAAGACCACCGCGATGCCCTCCGTGTAGTTCTGACCCTCGGGCCGGGTCGGGCAGCGGC
GCGGCTGCTCGAACTGCACCACCGTGGCGCCCGTGGGGGTGGGCACACGTAAAAGTTTGCATCGGTGTTCTCCG
CCTTGATGTCCCGCAGGTGCTCGCGCAGGGTGGCGTGGCCCGCGGCGACGGTCGCGTTGTCGCCGGCGGGGCGCG
GCGGCTTTGGGGGTTTCGGTTTTCTGTTCTTCTTCGGTTTCGGGTCCCCGTTGGGGGGCGCCAGGGGCGGGCG
GCGCCGGAGTGGCAGGGCCCCGTTCGCCGCCTGGGTCGCGGCCGCGACCCCAGGCGTGCCGGGGGAACTCGGAG
CCGCCGACGCCACCAGGACCCCCAGCGTCAACCCCAAGAGCGCCCATACGACGAACCACCGGCGCCCCGCGCGG
GGGCGCCCTGGCGCAT
```

FIG. 2

```
CTTAGAGCTCGTCTTCGTCTCCGGCCTCGTCCTCGTTGTGGAGCGGAGAGTACCTGGCTTTGTTGCGCTTGCGCA
GAACCATGTTGGTGACCTTGGAGCTGAGCAGGGCGCTCGTGCCCTTCTTTCTGGCCTTGTGTTCCGTGCGCTCCA
TGGCCGACACCAAAGCCATATATCGGATCATTTCTCGGGCCTCGGCCAACTTGGCCTCGTCAAACCCGCCCCCCT
CCGCGCCTTCCTCCCCCTCCCCGCCCACGCCCCGGGGTCGGAAGTCTTGAGTTCCTTGGTGGTGAGCGGATACA
GGGCCTTCATGGGATTGCGTTGCAGTTGCAGGACGTAGCGGAAGGCGAAGAAGGCCGCGACCAGGCCGGCCAGGA
CCAGCAGCCCCACGGCAAGCGCCCCGAAGGGGTTGGACATAAAGGAGGACACGCCCGAGACGGCCGACACCACGC
CCCCCACTACTCCCATGACTACCTTGCCGACCGCGCGCCCCAAGTCCCCCATCCCCTCGAAGAACGCGCACAGCC
CCGCGAACATGGCGGCGTTGGCGTCGGCGCGGATGACCGTGTCGATGTCGGCAAAGCGCAGGTCGTGCAGCTGGT
TGCGGCGCTGGACCTCCGTGTAGTCCAGCAGGCCGCTGTCCTTGATCTCGTGGCGCGTGTAGACCTCCAGGGGCA
CAAACTCGTGGTCCTCCAGCATGGTGATGTTCAGGTCGATGAAGGTGCTGACGGTGGTGACGTCGGCGCGACTCA
GCTGGTGAGAGTACGCGTACTCCTCGAAGTACACGTAGCCCCCGCCGAAGATGAAGTAGCGCCGGTGGCCCACGG
TGCACGGCTCGAGCGCGTCGCGGGTGAGGCGCAGCTCGTTGTTCTCGCCCAGCTGCCCCTCGATCAGCGGGCCCT
GGTCTTCGTACCGAAAGCTGACCAGGGGGCGGCTGTAGCACGTCCCCGGCCGCGAGCTGACGCGCATCGAGTTCT
GCACGATCACGTTGTCCGGGGCGACGGGCACGCACGTGGAGACGGCCATGACGTCTCCGAGCATGCGCGCGCTCA
CCCGCCGGCCGACGGTGGCGGAGGCGATGGCGTTGGGGTTGAGCTTGCGGCCTCGTTCCAGAGAGTCAGCTCGT
GGTTCTGCAGCTCGCACCACGCGACGGCGATGCGCCCCAGCATGTCATTCACGTGGCGCTGTATGTGGTTATACG
TAAACTGCAGCCGGGCGAACTCGATCGAGGAGGTGGTCTTGATGCGCTCCACGGACGCGTTGGCGCTGGGCGCCT
CCCGCAGTGGCGCGGGCGTGGCATTCCGGGGCTTGCGGTCCTGCTCCCGCATGTACTCCCGCACGTACAGCTCGG
CGAGCGTGTTGCTGAGGAGGGGCTGGTACGCGATGAGGAAGCCCCCGTGGCCAGGTAGTACTGCGGCTGGCCCA
CCTTGATGTGCGTGGCGTTGTACTTGCGCGCAAACATGCGGTCGATGGCCTCGCGGGCATCCCGGCCGATGCAGT
CGCCCAGGTCGACGCGCGAGAGCGAGTACTCGGTCAGGTTGGTGGTGAAGGTGGTCGAGATGGCGTCGGAGGAGA
AGCGGAAGGAGCCGCCGTACTCGGCGCGGAGCATCTCGTCCACCTCCTGCCACTTGGTCATGGTGCAGACCGCCG
GTCGCTTCGGCACCCAGTCCCAGGCCACGGTAAACTTGGGGGTCGTCAGCAAGTTGCGGGTCGTCGGCGACGTGG
CCCGGGCCTTCGTGGTGAGGTCGCGCGCGTAGAAGCCGTCGACCTGCTTGAAGCGGTCGGCGGCGTAGCTGGTGT
GCTCGGTGTGCGACCCCTCCCGGTAGCCGTAAAACGGGGACATGTACACAAAGTCGCCCGTCGCCAGCACAAACT
CATCGTACGGGTACACCGACCGCGCGTCCACCTCCTCGACGATGCAGTTGACCGTCGTGCCGTACCGATGGAACG
CCTCCACCCGCGAGGGGTTGTACTTGAGGTCGGTGGTGTGCCACCCCCGGCTCGTGCGCGTGGCGACCTTCGCCG
GCTTGAGCTCCATGTCGGTCTCGTGGTCGTCCCGGTGAAACGCGGTGGTCTCCATGTTGTTCCGCACGTACTTGG
CCGTGGAGCGGCAGACCCCCTTGGTGTTAATCTTGTCGATCACCTCCTCGAAGGGAACGGGGGCGCGGTCCTCGA
ATATCCCCATAAACTGGGAGTAGCGGTGGCCGAACCACACCTGCGACACGGTCACGTCTTTGTAGTACATGGTGG
CCTTGAATTTGTACGGGGCGATGTTCTCCTTGAAGACCACCGCGATGCCCTCCGTGTAGTTCTGCCCCTCCGGGC
GCGTCGGGCAGCGGCGCGGCTGCTCAAACTGCACCACCGTGGCGCCCGTCGGGGCGGGCACACGTAAAACTGGG
CATCGGCGTTCTCGACCTTGATTTCCCGCAGGTGCGCGCGCAGCGTGGCGTGGCCGGCGGCGACGGTCGCGTTGG
CGTCGGGGGCGGGTCGCCTCGGGCCGCTTGGGCGGCTTTTGGTTTTCCGCTTCCGGGCCTTGGTGGTCGCGG
GGCTCGGGACGGGGGCGGCCGGGAGGCGGGACCCCGTTCGCCGCGACGGTCGCGGCCACGCCGCCCGAGGCGC
GGGGGGCCGCCGGGGCCGCCGGGGCCGCCGACGCCACCGCGGCCACCAGCGCCCCACGACCAGCGCGCAAATCA
AGCCCCCCCGCGCAT
```

FIG.3

ATGCGCCAGGGCGCCCCCGCGCGGGGGCGCCGGTGGTTCGTCGTATGGGCGCTCTTGGGGTTGACGCTGG
GGGTCCTGGTGGCGTCGGCGGCTCCGAGTTCCCCCGGCACGCCTGGGGTCGCGGCCGCGACCCAGGCGGC
GAACGGGGCCCTGCCACTCCGGCGCCGCCCGCCCCTGGCGCCCCCCAACGGGGGACCCGAAACCGAAG
AAGAACAGAAAACCGAAACCCCCAAAGCCGCCGCGCCCGCCGGCGACAACGCGACCGTCGCCGCGGGCC
ACGCCACCCTGCGCGAGCACCTGCGGGACATCAAGGCGGAGAACACCGATGCAAACTTTTACGTGTGCCC
ACCCCCCACGGGCGCCACGGTGGTGCAGTTCGAGCAGCCGCGCCGCTGCCCGACCCGGCCCGAGGGTCAG
AACTACACGGAGGGCATCGCGGTGGTCTTCAAGGAGAACATCGCCCCGTACAAGTTCAAGGCCACCATGT
ACTACAAAGACGTCACCGTTTCGCAGGTGTGGTTCGGCCACCGCTACTCCCAGTTTATGGGGATCTTTGA
GGACCGCGCCCCCGTCCCCTTCGAGGAGGTGATCGACAAGATCAACGCCAAGGGGGTCTGTCGGTCCACG
GCCAAGTACGTGCGCAACAACCTGGAGACCACCGCGTTTCACCGGGACGACCACGAGACCGACATGGAGC
TGAAACCGGCCAACGCCGCGACCCGCACGAGCCGGGGCTGGCACACCACCGACCTCAAGTACAACCCCTC
GCGGGTGGAGGCGTTCCACCGGTACGGGACGACGGTAAACTGCATCGTCGAGGAGGTGGACGCGCGCTCG
GTGTACCCGTACGACGAGTTTGTGTTGGCGACTGGCGACTTTGTGTACATGTCCCCGTTTTACGGCTACC
GGGAGGGGTCGCACACCGAACACACCAGCTACGCCGCCGACCGCTTCAAGCAGGTCGACGGCTTCTACGC
GCGCGACCTCACCACCAAGGCCCGGGCCACGGCGCCGACCACCCGGAACCTGCTCACGACCCCCAAGTTC
ACCGTGGCCTGGGACTGGGTGCCAAAGCGCCCGTCGGTCTGCACCATGACCAAGTGGCAGGAGGTGGACG
AGATGCTGCGCTCCGAGTACGGCGGCTCCTTCCGATTCTCTTCCGACGCCATATCCACCACCTTCACCAC
CAACCTGACCGAGTACCCGCTCTCGCGCGTGGACCTGGGGGACTGCATCGGCAAGGACGCCCGCGACGCC
ATGGACCGCATCTTCGCCCGCAGGTACAACGCGACGCACATCAAGGTGGGCCAGCCGCAGTACTACCTGG
CCAATGGGGGCTTTCTGATCGCGTACCAGCCCCTTCTCAGCAACACGCTCGCGGAGCTGTACGTGCGGGA
ACACCTCCGCGAGCAGAGCCGCAAGCCCCCAAAACCCCACGCCCCCGCCGCCCGGGGCCAGCGCCAACGCG
TCCGTGGAGCGCATCAAGACCACCTCCTCCATCGAGTTCGCCAGGCTGCAGTTTACGTACAACCACATAC
AGCGCCATGTCAACGATATGTTGGGCCGCGTTGCCATCGCGTGGTGCGAGCTGCAGAATCACGAGCTGAC
CCTGTGGAACGAGGCCCGCAAGCTGAACCCCAACGCCATCGCCTCGGCCACCGTGGGCCGGCGGGTGAGC
GCGCGGATGCTCGGCGACGTGATGGCCGTCTCCACGTGCGTGCCGGTCGCCGCGGACAACGTGATCGTCC
AAAACTCGATGCGCATCAGCTCGCGGCCCGGGGCCTGCTACAGCCGCCCCCTGGTCAGCTTTCGGTACGA
AGACCAGGGCCCGTTGGTCGAGGGGCAGCTGGGGGAGAACAACGAGCTGCGGCTGACGCGCGATGCGATC
GAGCCGTGCACCGTGGGACACCGGCGCTACTTCACCTTCGGTGGGGCTACGTGTACTTCGAGGAGTACG
CGTACTCCCACCAGCTGAGCCGCGCCGACATCACCACCGTCAGCACCTTCATCGACCTCAACATCACCAT
GCTGGAGGATCACGAGTTTGTCCCCCTGGAGGTGTACACCCGCCACGAGATCAAGGACAGCGGCCTGCTG
GACTACACGGAGGTCCAGCGCCGCAACCAGCTGCACGACCTGCGCTTCGCCGACATCGACACGGTCATCC
ACGCCGACGCCAACGCCGCCATGTTTGCGGGCCTGGGCGCGTTCTTCGAGGGGATGGGCGACCTGGGGCG
CGCGGTCGGCAAGGTGGTGATGGGCATCGTGGGCGGCGTGGTATCGGCCGTGTCGGGCGTGTCCTCCTTC
ATGTCCAACCCCTTTGGGGCGCTGGCCGTGGGTCTGTTGGTCCTGGCCGGCCTGGCGGCGGCCTTCTTCG
CCTTTCGCTACGTCATGCGGCTGCAGAGCAACCCCATGAAGGCCCTGTACCCGCTAACCACCAAGGAGCT
CAAGAACCCCACCAACCCGGACGCGTCCGGGGAGGGCGAGGAGGGCGGCGACTTTGACGAGGCCAAGCTA
GCCGAGGCCCGGGAGATGATACGGTACATGGCCCTGGTGTCTGCCATGGAGCGCACGGAACACAAGGCCA
AGAAGAAGGGCACGAGCGCGCTGCTCAGCGCCAAGGTCACCGACATGGTCATGCGCAAGCGCCGCAACAC
CAACTACACCCAAGTTCCCAACAAAGACGGTGACGCCGACGAGGACGACCTGTGAT

FIG.4

```
ATGCGCGGGGGGGGCTTGATTTGCGCGCTGGTCGTGGGGGCGCTGGTGGCCGCGGTGGCGTCGGCGGCCC
CGGCGGCCCCGGCGGCCCCCCGCGCCTCGGGCGGCGTGGCCGCGACCGTCGCGGCGAACGGGGGTCCCGC
CTCCCGGCCGCCCCCGTCCCGAGCCCCGCGACCACCAAGGCCCGGAAGCGGAAAACCAAAAAGCCGCCC
AAGCGGCCCGAGGCGACCCCGCCCCCCGACGCCAACGCGACCGTCGCCGCCGGCCACGCCACGCTGCGCG
CGCACCTGCGGGAAATCAAGGTCGAGAACGCCGATGCCCAGTTTTACGTGTGCCCGCCCCCGACGGGCGC
CACGGTGGTGCAGTTTGAGCAGCCGCGCCGCTGCCCGACGCGCCCGGAGGGGCAGAACTACACGGAGGGC
ATCGCGGTGGTCTTCAAGGAGAACATCGCCCCGTACAAATTCAAGGCCACCATGTACTACAAAGACGTGA
CCGTGTCGCAGGTGTGGTTCGGCCACCGCTACTCCCAGTTTATGGGGATATTCGAGGACCGCGCCCCCGT
TCCCTTCGAGGAGGTGATCGACAAGATTAACACCAAGGGGGTCTGCCGCTCCACGGCCAAGTACGTGCGG
AACAACATGGAGACCACCGCGTTTCACCGGGACGACCACGAGACCGACATGGAGCTCAAGCCGGCGAAGG
TCGCCACGCGCACGAGCCGGGGTGGCACACCACCGACCTCAAGTACAACCCCTCGCGGGTGGAGGCGTT
CCATCGGTACGGCACGACGGTCAACTGCATCGTCGAGGAGGTGGACGCGCGGTCGGTGTACCCGTACGAT
GAGTTTGTGCTGGCGACGGGCGACTTTGTGTACATGTCCCCGTTTTACGGCTACCGGGAGGGGTCGCACA
CCGAGCACACCAGCTACGCCGCCGACCGCTTCAAGCAGGTCGACGGCTTCTACGCGCGCGACCTCACCAC
GAAGGCCCGGGCCACGTCGCCGACGACCCGCAACTTGCTGACGACCCCCAAGTTTACCGTGGCCTGGGAC
TGGGTGCCGAAGCGACCGGCGGTCTGCACCATGACCAAGTGGCAGGAGGTGGACGAGATGCTCCGCGCCG
AGTACGGCGGCTCCTTCCGCTTCTCCTCCGACGCCATCTCGACCACCTTCACCACCAACCTGACCGAGTA
CTCGCTCTCGCGCGTCGACCTGGGCGACTGCATCGGCCGGGATGCCCGCGAGGCCATCGACCGCATGTTT
GCGCGCAAGTACAACGCCACGCACATCAAGGTGGGCCAGCCGCAGTACTACCTGGCCACGGGGGGCTTCC
TCATCGCGTACCAGCCCCTCCTCAGCAACACGCTCGCCGAGCTGTACGTGCGGGAGTACATGCGGGAGCA
GGACCGCAAGCCCCGGAATGCCACGCCCGCGCCACTGCGGGAGGCGCCCAGCGCCAACGCGTCCGTGGAG
CGCATCAAGACCACCTCCTCGATCGAGTTCGCCCGGCTGCAGTTTACGTATAACCACATACAGCGCCACG
TGAATGACATGCTGGGGCGCATCGCCGTCGCGTGGTGCGAGCTGCAGAACCACGAGCTGACTCTCTGGAA
CGAGGCCCGCAAGCTCAACCCCAACGCCATCGCCTCCGCCACCGTCGGCCGGCGGGTGAGCGCGCGCATG
CTCGGAGACGTCATGGCCGTCTCCACGTGCGTGCCCGTCGCCCCGGACAACGTGATCGTGCAGAACTCGA
TGCGCGTCAGCTCGCGGCCGGGGACGTGCTACAGCCGCCCCCTGGTCAGCTTTCGGTACGAAGACCAGGG
CCCGCTGATCGAGGGGCAGCTGGGCGAGAACAACGAGCTGCGCCTCACCCGCGACGCGCTCGAGCCGTGC
ACCGTGGGCCACCGGCGCTACTTCATCTTCGGCGGGGGCTACGTGTACTTCGAGGAGTACGCGTACTCTC
ACCAGCTGAGTCGCGCCGACGTCACCACCGTCAGCACCTTCATCGACCTGAACATCACCATGCTGGAGGA
CCACGAGTTTGTGCCCCTGGAGGTCTACACGCGCCACGAGATCAAGGACAGCGGCCTGCTGGACTACACG
GAGGTCCAGCGCCGCAACCAGCTGCACGACCTGCGCTTTGCCGACATCGACACGGTCATCCGCGCCGACG
CCAACGCCGCCATGTTCGCGGGCTGTGCGCGTTCTTCGAGGGGATGGGGGACTTGGGGCGCGCGGTCGG
CAAGGTAGTCATGGGAGTAGTGGGGGGCGTGGTGTCGGCCGTCTCGGGCGTGTCCTCCTTTATGTCCAAC
CCCTTCGGGGCGCTTGCCGTGGGGCTGCTGGTCCTGGCCGGCCTGGTCGCGGCCTTCTTCGCCTTCCGCT
ACGTCCTGCAACTGCAACGCAATCCCATGAAGGCCCTGTATCCGCTCACCACCAAGGAACTCAAGACTTC
CGACCCCGGGGCGTGGGCGGGGAGGGGGAGGAAGGCGCGGAGGGGGCGGGTTTGACGAGGCCAAGTTG
GCCGAGGCCCGAGAAATGATCCGATATATGGCTTTGGTGTCGGCCATGGAGCGCACGGAACACAAGGCCA
GAAAGAAGGGCACGAGCGCCCTGCTCAGCTCCAAGGTCACCAACATGGTTCTGCGCAAGCGCAACAAAGC
CAGGTACTCTCCGCTCCACAACGAGGACGAGGCCGGAGACGAAGACGAGCTCTAAG
```

METHODS AND COMPOSITIONS RELATED THERETO FOR DETECTING AND IDENTIFYING DISTINCT SPECIES OF NUCLEIC ACIDS FROM CAUSATIVE AGENTS

Priority is derived from U.S. Provisional Application Ser. No. 60/616,723, filed Oct. 7, 2004, which disclosure is herein incorporated by reference.

FIELD OF THE INVENTION

The present invention relates to methods for ascertaining whether a sample includes a first nucleic acid-containing entity or a second nucleic acid-containing entity particularly in the field of clinical diagnostic services, i.e., in the industry of the detection and identification of biological agents associated with disease conditions.

BACKGROUND OF THE INVENTION

Clinical diagnostics provide an essential aid to the physician for the diagnosis and monitoring of numerous pathologies and infectious diseases. Rapid and accurate identification of causative agents of a myriad of different human pathophysiological conditions is a paramount requisite to effective treatment.

A biological sample generally is taken from the patient, most often at the request of a physician, and sent to a medical laboratory for analysis to establish or confirm a diagnosis of clinical symptoms. A physician may suspect a particular causative agent upon physical examination. However, certain symptoms may be characteristic of a plethora of different causative agents. Therefore, due to misdiagnoses of causative agents, patients may be treated non-efficaciously. Moreover, in other instances, a physician may request a certain diagnostic test to be performed on a clinical specimen wherein the test subsequently produces a negative result. Then, of course, further clinical samples and diagnostic testing is required. In many instances, due to the lack of timely and accurate diagnoses, patients' original conditions progress to the further detriment of treatability and to the well-being of the patient. Accurate clinical diagnosis is critical to specifically identify causative agents, and in many cases specific species of infectious agents which mediate pathophysiological conditions in a timely manner. Accordingly, a need indeed exists for methods for detecting and identifying distinct species, in a single container, from a genus of infectious agents.

Direct detection techniques for Herpes Simplex Virus (HSV), for example, can include viral culture, Tzanck's smear, antigen detection, direct fluorescent antibody analysis, and viral DNA detection. Cusini et al., 2001, J. Antimicrob. Chemother. 47 Suppl T1, 9-16.

The use of conventional PCR techniques with probe-based hybridization for the direct detection of HSV DNA have been reported for subtyping of clinical specimens. Cone et al., 1991, J. Infect. Dis. 164:757-60. Conventional PCR has significant advantages over viral culture procedures, as the virus does not have to be infective and HSV DNA can be detected in the late stages of genital lesions more efficiently. Lucotte et al., 1995, Mol. Cell Probes 9:287-90. Stocher et al. reported on the parallel detection of CMV, EBV, HSV-1, HSV-2, and VZV from cerebrospinal fluid, serum, and plasma samples utilizing the LightCycler real-time PCR technology. Stocher et al., 2003, J. Clin. Virol. 26:85-93. Two reports developed TaqMan assays for the parallel detection of members of the Herpesviridae family in multiple, separate assays and yet another two have reported on SYBR green real-time PCR assays for the parallel detection of HSV-1, HSV-2, or both in clinical specimens. van Doornum et al., 2003, J. Clin. Microbiol. 41:576-80; Weidmann et al., 2003, J. Clin. Microbiol. 41:1565-8; Nicoll et al., 2001, J. Virol. Methods 96:25-31; Schmutzhard et al., 2004, J. Clin. Virol. 29:120-6. A recent study, for example, was published which analyzed the presence of HSV in more than 36,000 mucosal secretions found the detection rate of HSV DNA by real-time PCR techniques to be 12.1% of the samples versus 3.0% detected by viral culture. The method employed, however, could not discriminate between HSV-1 and HSV-2. Wald et al., 2003, J. Infect Dis. 188:1345-51.

Particularly, the need exists in the industry for rapid and accurate methods for ascertaining whether a sample includes a first nucleic acid-containing entity or a second nucleic acid-containing entity, the ability, for example, to identify distinct species of nucleic acids corresponding to distinct species of infectious agents in a single container.

SUMMARY OF THE INVENTION

The present invention is directed to methods for ascertaining whether a sample includes a first nucleic acid-containing entity or a second nucleic acid-containing entity, comprising (a) providing a single vessel containing (1) a nucleic acid from the sample, (2) a forward primer, (3) a reverse primer, (4) a first probe specific to the first entity, and (5) a second probe specific to the second entity, wherein a combination comprising the forward primer and the reverse primer is capable of amplifying, by the polymerase chain reaction, a segment of the nucleic acid of (1) the first entity to produce a first amplicon, and (2) the second entity to produce a second amplicon, and wherein the nucleotide sequence of the first amplicon and the nucleotide sequence of the second amplicon are not identical, (b) incubating the vessel under conditions allowing production of (1) the first amplicon if the sample contains the first entity, and (2) the second amplicon if the sample contains the second entity, (c) detecting a first signal generated from the first probe if the first amplicon is produced in (b), and detecting a second signal generated from the second probe if the second amplicon is produced in (b), and (d) ascertaining that (1) the sample does not contain the first entity or the second entity if the first signal and the second signal are not detected in (c), (2) the sample contains the first entity and does not contain the second entity if the first signal is detected in (c) and the second signal is not detected in (c), (3) the sample does not contain the first entity and contains the second entity if the first signal is not detected in (c) and the second signal is detected in (c), or (4) the sample contains the first entity and the second entity if the first signal and the second signal are detected in (c).

In addition, the current invention is directed to methods for ascertaining whether a sample includes a first nucleic acid-containing entity or a second nucleic acid-containing entity wherein both the first nucleic acid-containing entity and a second nucleic acid-containing entity are members of the Herpesviridae family.

The invention is further directed to methods wherein the first entity is HSV-1, and wherein the second entity is HSV-2, for example, wherein the first amplicon and the second amplicon contain at least a segment of the open reading frame of a gene encoding a glycoprotein, e.g., glycoprotein B.

Further, the invention is directed to compositions for the detection and distinct identification of HSV-1 and HSV-2 comprising a first oligonucleotide primer, at least 8 nucleotides in length, common to a region within positions 978 to 1149 (5-3') of SEQ ID NO:2 and the corresponding homolog region of SEQ ID NO:1 and, a second oligonucleotide primer, at least 8 nucleotides in length, that is common to a region within positions 1348 to 1546 (5-3') of SEQ ID NO:3 and the corresponding homolog region of SEQ ID NO:4, and a first oligonucleotide probe between about 15 and about 40 nucleotides in length specific to a sequence selected from the group consisting of SEQ ID NO:1 and SEQ ID NO:3 and a second oligonucleotide probe between about 15 and about 40 nucleotides in length specific to a sequence selected from the group consisting of SEQ ID NO:2 and SEQ ID NO:4, wherein the first and second oligonucleotide probes are each detectably labeled with distinctly different detectable labels.

BRIEF DESCRIPTION OF THE FIGURES

FIG. 1 displays SEQ ID NO:1 (reverse complement of HSV-1 coding region for glycoprotein B), an example distinct species of nucleic acid from a certain genus of infectious agents (HSV-1 and HSV-2).

FIG. 2 displays SEQ ID NO:2 (reverse complement of HSV-2 coding region for glycoprotein B), an example distinct species of nucleic acid from a certain genus of infectious agents (HSV-1 and HSV-2).

FIG. 3 displays SEQ ID NO:3 (HSV-1 coding region for glycoprotein B), an example distinct species of nucleic acid from a certain genus of infectious agents (HSV-1 and HSV-2).

FIG. 4 displays SEQ ID NO:4 (HSV-2 coding region for glycoprotein B), an example distinct species of nucleic acid from a certain genus of infectious agents (HSV-1 and HSV-2).

DETAILED DESCRIPTION OF THE INVENTION

Unless defined otherwise, all technical and scientific terms used herein have the same meaning as is commonly understood by one of skill in the art to which this invention belongs. All publications and patents referred to herein are incorporated by reference.

Physicians are generally faced with observing patients' symptoms, obtaining biological samples, and ordering clinical diagnostic tests to determine the identity of causative agents which mediate pathological conditions. Since methods of treatment of pathophysiological conditions are intimately related to the species of the causative agent(s) of the condition, rapid and accurate identification and reporting of the species of causative agent(s) is of paramount importance in many cases to the practice of medicine today. The present invention enables the accurate and rapid detection and identification of distinct species of nucleic acids from a genus of causative agents derived from each clinical sample.

An embodiment of the present invention, for example, is a method for ascertaining whether a sample includes a first nucleic acid-containing entity or a second nucleic acid-containing entity, wherein the method comprises, (a) providing a single vessel containing (1) a nucleic acid from the sample, (2) a forward primer, (3) a reverse primer, (4) a first probe specific to the first entity, and (5) a second probe specific to the second entity, wherein a combination comprising the forward primer and the reverse primer is capable of amplifying, by the polymerase chain reaction, a segment of the nucleic acid of (1) the first entity to produce a first amplicon, and (2) the second entity to produce a second amplicon, and wherein the nucleotide sequence of the first amplicon and the nucleotide sequence of the second amplicon are not identical, (b) incubating the vessel under conditions allowing production of (1) the first amplicon if the sample contains the first entity, and (2) the second amplicon if the sample contains the second entity, (c) detecting a first signal generated from the first probe if the first amplicon is produced in (b), and detecting a second signal generated from the second probe if the second amplicon is produced in (b), and (d) ascertaining that (1) the sample does not contain the first entity or the second entity if the first signal and the second signal are not detected in (c), (2) the sample contains the first entity and does not contain the second entity if the first signal is detected in (c) and the second signal is not detected in (c), (3) the sample does not contain the first entity and contains the second entity if the first signal is not detected in (c) and the second signal is detected in (c), or (4) the sample contains the first entity and the second entity if the first signal and the second signal are detected in (c).

Exemplary methods are wherein the first entity is a first strain of a herpesvirus (i.e., a member of the Herpesviridae family), and wherein the second entity is a second strain of a herpesvirus. For example, wherein the first entity is HSV-1, and wherein the second entity is HSV-2.

The present invention includes but is not limited to PCR methods as well as primers and probes for detecting and specifically identifying and discriminating the presence of HSV-1 and HSV-2 in a sample in a single tube reaction, for example.

Exemplified herein is the design and validation of an example real-time PCR assay capable of simultaneously detecting each HSV subtype. Particularly, methods of the present invention are provided for detecting and specifically identifying and discriminating the presence of HSV-1 and HSV-2 in a sample in a single tube reaction. The methods are applied, for example, in the detection of HSV-1 and/or HSV-2 in a biological sample from a patient. An example presented herein particularly employ a pair of PCR amplification primers wherein each primer is homologous to a glycoprotein B coding region of both HSV-1 and HSV-2 but which also flank and thereby target divergent sequences in the viral subtypes for amplification. Separate probes are employed which correspond to distinct HSV-1 and HSV-2 nucleic acid sequences within the divergent amplified regions. Accordingly, example reagents, i.e., primers and probes are provided. Separate labels and separate quenchers, discussed infra, are employed in connection with each of the probes in the example presented herein. Real-time methods are preferred embodiments of the present invention. Methods of the invention are a significantly more sensitive clinical diagnostic technique capable of detecting and specifically identifying and discriminating the presence of HSV-1 and HSV-2, for example, in a single reaction tube while providing accurate results in a fraction of the time of viral culture and conventional PCR methods.

The example described herein validated an example combination of primers and dual-labeled oligonucleotide probes for the type-specific detection of HSV DNA in a single reaction.

Exemplary Illustration of an Embodiment of the Invention

One embodiment of the present invention is a multiplex real-time PCR assay developed to simultaneously detect HSV-1 and/or HSV-2 on a Rotor-Gene 3000 platform, for example. Subtyping validation in this example was performed by Pyrosequencing to obtain short sequences of nucleotides capable of identifying HSV-1 and/or HSV-2 DNA. This technique was applied to 4,581 cervicovaginal swabs sampled from women primarily from six states. The prevalence of HSV detection in these specimens is presented to illustrate an example application of the general methods of the present invention.

Confirmed positive HSV-1 and HSV-2 samples purchased from the American Type Culture Collection (ATCC) and HSV-1 and HSV-2 infected clinical specimens were assayed simultaneously with shared amplification primers and subtype-specific probes against the HSV glycoprotein B gene on a Rotor-Gene 3000 platform. A distinct set of primers towards heterogeneous genes of HSV was avoided to minimize cross-reactivities, which could be inherent to the incorporation of four oligonucleotide primers and two dual-labeled probes into a single reaction. Separately, two PCR reactions were performed in which one primer contained a 5' biotinylated modification. Single-stranded DNA from the amplicon was purified and Pyrosequenced.

The quantitative range of the assay extended from $10^8$ through 10 copies of each virus ($r^2>0.991$) and specificity was determined by non-amplification of 37 different human pathogens, including other herpesviruses such as VZV, CMV, and EBV. Sensitivity and specificity values of 100% were calculated by concordance analysis between the real-time PCR and the DNA Pyrosequencing results (HSV-1: n=119, HSV-2: n=120). Application of this assay to 4,581 cervicovaginal swab specimens collected from women visiting physicians primarily in six states provided detection rates of 3.1% for HSV-1 and 7.6% for HSV-2. The average age of women infected with HSV-1 was 29.5 versus 35.6 for HSV-2. Of the 4,581 cervical swab DNA specimens analyzed for the presence of HSV-1 or HSV-2 DNA by this testing procedure, 479 (10.5%, 95% CI, 9.61-11.4%) were determined to be positive for either subtype. This compared to 1,779 of 10,974 positive HSV specimens (16.2%; 95% CI, 15.5-16.9%) collected in the Puget Sound area in Washington and 24% and 36% of 110 clinical dermal or genital lesion specimens from patients with suspected mucocutaneous HSV infections which were positive for HSV-1 and HSV-2, respectively, in another study in which the sequence-unspecific SYBR green dye was incorporated into a real-time PCR reaction. Wald et al., 2003, J. Infect. Dis. 188:1345-51; Schmutzhard et al., 2004, J. Clin. Virol 29:120-6. Of the 4,581 clinical cervical swab specimens analyzed, none were determined to simultaneously contain both HSV-1 and HSV-2. An analysis of the NHANES III data reported that 16.6% of the 13,904 American individuals tested were seropositive for both HSV-1 and HSV-2, although this statistic does not indicate if lesions indicative of infection from both viruses were present simultaneously. With respect to infection by both viral herpes subtypes, some studies have suggested an initial infection with HSV-1 reduces the likelihood that a subsequent HSV-2 infection will be symptomatic. Xu et al., 2002, J. Infect. Dis. 185:1019-24.

Real-time PCR is a proven advancement over conventional PCR as the decrease in turn-around time is even more pronounced as the need for time-consuming agarose gel separation techniques is obviated. Some platforms, like the Rotor-Gene 3000 used in this study, operate as a closed-tube system and coupled with enzymes like uracil-DNA glycosylase (UNG) can further reduce the possibility of carryover contamination. The example of the present invention presented herein is a real-time PCR assay which is both highly sensitive and specific for the simultaneous subtype-specific detection of both HSV-1 and HSV-2 DNA in a single reaction.

Pyrosequencing was utilized in an example embodiment presented herein as a rapid and innovative nucleic acid based sequencing solution for validating the identity of the HSV subtype in a clinical specimen. A heterogeneous region was sequenced to readily distinguish one subtype from another as an alternative to immunofluorescence screening of viral cultures with subtype-specific antisera. Pyrosequencing is amenable to a 96 well format permitting the simultaneous screening of a large number of specimens and is also rapid in that once a run is initiated, approximately one nucleotide can be dispensed per minute with real-time data acquisition and interpretation. When the Pyrosequencing analysis of clinical specimens was used as a standard, 100% sensitivity and specificity for both HSV-1 and HSV-2 were calculated. This validation procedure used in conjunction with the described real-time PCR exemplifies an embodiment of the present invention for the simultaneous direct molecular detection of both subtypes of HSV DNA.

Example HSV-1 and HSV-2 Primers and Probes

The oligonucleotide primers and probes specifically employed in a certain embodiment of the invention presented herein were synthesized by Integrated DNA Technologies (IDT, Coralville, Iowa) and are listed in Table I. The dual-labeled oligonucleotide probes and 5' biotinylated primers were purified by high performance liquid chromatography (HPLC) by the manufacturer.

TABLE II

Example Primer and probe sequences for real-time PCR amplification and detection of HSV-1 and HSV-2

| Primer | Sequence 5' to 3' |
| --- | --- |
| HSV1/2 FOR | TTCTGCAGCTCGCACCAC (SEQ ID NO:5) |
| HSV1/2 REV | GGAGCGCATCAAGACCACC (SEQ ID NO:6) |
| HSV1Pr | 6-carboxyfluorescein/ CGATGGCAACGCGGCCCAACATATCGTTGAC (SEQ ID NO:7)/BHQ-1 |
| HSV2Pr | Cy5/CGATGCGCCCCAGCATGTCGTTCACGT (SEQ ID NO:8)/BHQ-2 Cy5/CGATGCGCCCCAGCATGTCATTCACGT (SEQ ID NO:9)/BHQ-2 |
| HSV2a-1 (Cone et al., 1991) | CTGGTCAGCTTTCGGTACGA (SEQ ID NO:10) |
| HSV2a-2 (Cone et al., 1991) | CAGGTCGTGCAGCTGGTTGC (SEQ ID NO:11) |
| HSVcv-seq1 | CCTTGATCTCGTGGC (SEQ ID NO:12) |

Primers and probes (nucleic acid reagents) for employment in methods of the present invention are herein expressly not limited to those exemplified in Table I. The following discussion of example reagents for use in methods of the present invention particularly refers to FIG. 1 (SEQ ID NO:1), FIG. 2 (SEQ ID NO:2), FIG. 3 (SEQ ID NO:3), and FIG. 4 (SEQ ID NO:4) attached hereto, nucleic acids (positions 1-2716) HSV-1 and HSV-2 corresponding to respective regions of each subtype for glycoprotein B. See, e.g., NCBI accession Nos.

Primers

The "HSV1/2 FOR" (forward) primer (SEQ ID NO:5) exemplified in Table I, for example, is derived from a homolog portion of the reverse complement sequence of the HSV-1 and HSV-2 coding region for glycoprotein B that is common to both species (i.e., the homologous genes are identical in sequence at that site). The HSV-2 reverse complement of the coding region for glycoprotein B is shown in FIG. 2 (SEQ ID NO:2). SEQ ID NO:5 is the same as positions 1128-1145 of SEQ ID NO:2. The corresponding homologous region of the HSV-1 reverse complement of the coding region for glycoprotein B are positions 1119-1136 of SEQ ID NO:1 (FIG. 1). Accordingly, SEQ ID NO:5 is the same as positions 1119-1136 of SEQ ID NO:1.

The "HSV1/2 REV" (reverse) primer (SEQ ID NO:6) exemplified in Table I, for example, is derived from a homologous portion, i.e., 'common to' or identical in sequence, of the HSV-1 and HSV-2 coding region for glycoprotein B. The HSV-1 coding region for glycoprotein B is shown in FIG. 3 (SEQ ID NO:3). SEQ ID NO:6 is the same as positions 1476-1494 of SEQ ID NO:3. The corresponding homologous region of the HSV-2 coding region for glycoprotein B are positions 1467-1485 of SEQ ID NO:4 (FIG. 4). Accordingly, SEQ ID NO:6 is the same as positions 1467-1485 of SEQ ID NO:4.

Accordingly, example target regions of HSV-1 and HSV-2 nucleic acids, i.e., respective glycoprotein B regions, correspond to positions 1128 to about position 1250 of SEQ ID NO:2. This target region for amplification is therefore at least about 118-125 nucleotide bases in length, e.g., 122, nucleotides in length. Target regions of the present invention comprise, for example, positions 1131-1240 of SEQ ID NO:2. The art of selection and synthesis of PCR primers in order to amplify a particular target sequence is indeed well-known to those of ordinary skill in the art. Typically, oligonucleotide primers are about 8 to about 50 nucleotides in length (e.g., 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length). Primers 12 to 24 nucleotides in length are preferred. Primer pairs that amplify particular nucleic acid molecules, e.g., both HSV-1 and HSV-2 regions less than about 410 bases in length (preferably less than about 250 bases in length) that comprise, for example, or correspond to positions 1131-1240 of SEQ ID NO:2, can be designed using, for example, a computer program such as OLIGO (Molecular Biology Insights, Inc., Cascade, Colo.). Important features in choosing primers to target HSV-1 and HSV-2 regions of the present invention, for example, include that both the forward and reverse primers, although not necessary, per se, are preferably consensus, i.e., homologous (identical matches or exactly complementary in the case of reverse primers) to both HSV-1 and HSV-2 coding regions of glycoprotein B.

In addition to what is discussed supra, an important factor in the success of this embodiment of the present invention is that the primers function in PCR to amplify HSV-1 and HSV-2 regions less than about 410 bases in length that comprise, for example, positions 1131-1240 of SEQ ID NO:2. Accordingly, another HSV-1 and HSV-2 preferred target region of the present invention, for example, with reference to SEQ ID NO:2, for example, comprises a nucleic acid sequence which extends from about position 1011, 1010, 1009, 1008, 1007, 1006, 1005, 1003, or 1002 to about position 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, or 1269. Another HSV-1 and HSV-2 preferred target region of the present invention, for example, with reference to SEQ ID NO:2, comprises a nucleic acid sequence which extends from about position 980, 979 or 978 to about position 1380, 1381, 1382, 1383 or 1384. The Applicants point out, however, that primers corresponding to each of the 5' and 3' terminal portions of the various target regions of HSV-1 and HSV-2 target nucleic acids discussed herein may be combined with each other. Accordingly, all primers disclosed, suggested, and contemplated herein are each independently regarded as novel compositions of matter that can be employed pairwise to amplify HSV-1 and HSV-2 regions at least about 110 bases in length but less than about 410 bases in length that comprise, for example, the region corresponding to positions 1131-1240 of HSV-2 as indicated in SEQ ID NO:2.

Probes

Nucleic acid probes for use in methods of the present invention are preferably within the range of about 15 to about 50 nucleotides in length. More preferred probes are generally within the range of about 20 to about 40 nucleotides in length.

Particularly preferred probes for use in methods of the present invention comprise positions 1154 to 1169 of SEQ ID NO:2 or the complement thereof as well as a probe specific to the corresponding homolog region of SEQ ID NO:1 or an exact complement thereof. The "HSV1Pr" (HSV-1 probe) exemplified in Table I, for example, is derived from the target region of HSV-1 shown in SEQ ID NO:1 (positions 1138-1168) (corresponding to SEQ ID NO:2 homolog positions 1147-1173). Many different HSV-1 probes may be employed in methods of the present invention to selectively hybridize to the amplified HSV-1 target region. Derivative probes of the HSV-1 probe shown in Table I, for example, may be constructed by extending and/or truncating the exemplified species, in view of FIG. 1, at either/or both the 5' and 3' ends.

Example HSV-2 probes for use in methods of the present invention comprise SEQ ID NO:2 positions 1160 to 1175 of HSV-2 or homolog positions corresponding thereto. The "HSV2Pr" (HSV-2 probes) exemplified in Table I, for example, is derived from the target region of HSV-2 (SEQ ID NO:2), e.g., corresponding to positions 1153-1179. Many different HSV-2 probes may be employed in methods of the present invention to selectively hybridize to the amplified HSV-2 target region. Derivative probes of the HSV-2 probes shown in Table I, for example, may be constructed by extending and/or truncating the exemplified species, in view of SEQ ID NO:2, for example.

Detectable labels and quenchers indicated in Table I in association with the exemplified probes are readily substituted by any of a myriad of similar functional entities now well-known to those of ordinary skill in the art.

Real-Time PCR Amplification Parameters

Each 25 μl reaction contained 0.5 μg extracted DNA, 0.90 μM HSV1/2 FOR, 0.90 μM HSV1/2 REV, 0.2 μM HSV1Pr, 0.05 μM HSV2Pr, and 1xqPCR mastermix (Eurogentec, San Diego, Calif.) which contains dNTP/dUTP, Hot Goldstar DNA polymerase, $MgCl_2$, and uracil-DNA glycosylase (UNG). The real-time PCR reactions were performed on a Rotor-Gene 3000 instrument (Corbett Research, Mortlake, Australia) and included an initial incubation at 50° C. for 2 min for UNG activity followed by 95° C. for 10 min to inactivate the UNG, activate the Hot Goldstar DNA polymerase, and initially denature the DNA. Next, 35 cycles of denaturation (95° C., 15 sec) and annealing/extension (55° C., 45 sec) were performed with consecutive acquisition at 470 nm source/510 nm detection (HSV1Pr) and 625 nm source/660 hp detection (HSV2Pr) immediately following each annealing/extension step. Analysis was performed with the Rotor-Gene 3000 Software, Version 5 (Build 47) with slope correction and reaction efficiency threshold enabled and the negative template control (NTC) threshold set to a maximum of 10%. The amplification target for both viruses is the HSV glycoprotein B gene and successful amplification would result in a 122 by product. Positive results from clinical specimens were confirmed by repeating the initial reaction in two separate reactions, each with a single dual-labeled probe and fluorescence acquisition tailored to the respective fluorophore.

Pyrosequencing

Pyrosequencing is a bioluminescent sequencing procedure permitting the identification of short oligonucleotide segments of DNA up to 100 nucleotides in length (Gharizadeh et al., 2002, Anal. Biochem. 301(1):82-90; Ronaghi et al., 1998, Science. 281(5375):363-5.). A Pyrosequencing procedure was used to identify PCR positive amplicons as either HSV-1 or HSV-2 for comparison with the subtype-specific real-time PCR reactions. For single-stranded DNA purification prior to Pyrosequencing analysis, the HSV1/2 Rev and HSV2a-1 primers were each synthesized with a 5' biotin label which was incorporated into the amplicon during the amplification process. The biotinylated PCR product was captured with streptavidin Sepharose and purified with a vacuum prep workstation according to the manufacturer's instructions (Biotage, Uppsala, Sweden). For the Pyrosequencing reaction, HSVcv-seq1 was utilized to prime the 5' biotin-HSV2a-1 and HSV-2a-2 amplification product and HSV1/2 FOR was used to sequence the 5' biotin-HSV1/2 REV and HSV1/2 FOR amplicons. A Pyrosequencing 96MA System was programmed with a directed nucleotide dispensation order of TGCGATCTGCGACTCG for the real-time PCR primers and 15 cycles of a repetitive ATCG dispensation order for amplicons derived from conventional PCR primer amplification. The resulting pyrograms were analyzed with the PSQ 96MA version 2.0.2 software.

Precautions Against Contamination

Extraction of DNA, preparation of the PCR reactions, amplification in the Rotor-Gene 3000 machines, and the Pyrosequencing procedures were each performed in physically separate rooms. Pyrogen-free, nuclease-free water was used in the isolation of DNA from the cervicovaginal swabs and ATCC extracted controls. New Finn pipettes were used solely with filter tips for PCR. PCRs were each prepared in a UV-irradiated PCR biohood and UNG was incorporated into the Eurogentec PCR mastermix to minimize, if not eliminate, the possibility of carry-over contamination (Poljak et al., 1998, J. Virol. Methods. 71(1):1-6.).

Statistical Analysis

Mean values are presented with standard deviations (SD). Two-sided 95% confidence intervals (95% CI) were calculated using the Wilson procedure (Newcombe, 1998. Stat. Med. 17(8). 857-72.). All calculations were performed using Microsoft Excel v.X, VassarStats (Lowry, 1998-2002, 2004: www.vassarstats.com), and GraphPad Instat version 3.0b for Macintosh (GraphPad Software, San Diego, Calif.).

Sensitivity

For each HSV target, a positive vector control was generated as described in Example III. Spectrophotometric analysis was utilized to determine the plasmid concentration and serial dilutions from $1\times10^8$ through 10 copies of each vector were added as template in triplicate. Fluorescent signal acquisition was performed consecutively during the same reaction in two different channels, 6-carboxyfluorescein for HSV-1 (HSV1Pr probe) and Cy5 for HSV-2 (HSV2Pr probe). Linear regression analysis of the cycle threshold ($O_T$) values demonstrating the quantitative capacity of the assay; $r^2$ values of 0.991 and 0.999 were calculated for the HSV-1 and HSV-2 probes, respectively. One observation with this assay was a quantitative inability to detect a signal from one HSV type when the other subtype is present in the same reaction by a difference of three orders of magnitude or more. If both were present in concentrations that differed by less than this, either at high or low quantities, the detection capacity was unaffected.

Specificity

NCBI BLAST analysis (Altschul et al., 1997, Nucleic Acids Res. 25(17):3389-402.) of the amplification primer and dual-labeled probe nucleotide sequences against the GenBank "nr" nucleotide database revealed HSV-1 and HSV-2 as the only identical matches. As the GenBank database is incomplete and the specificity of the amplification procedure is of the highest priority for clinical diagnostics, DNA was extracted from 37 human pathogens of viral, bacterial, and fungal origin (Table II) purchased from American Type Cultures Collection (ATCC). DNA from each was tested for cross-reactivity and none was detectable. Whereas both the HSV-1/2 Rev+For and HSV2a-1+2 primer combinations will amplify HSV-1 and HSV-2, the dual-labeled probes were designed to discriminate between the two viruses. The HSV-1 probe was designed such that only 12 of 31 nucleotides (38.7%) were complementary to the HSV-2 genome while the HSV-2 probe has only 12 of 27 nucleotides (44.4%) complementary to HSV-1. As a result in all analyses, the HSV-1 template DNA was not detectable by the HSV-2 probe in the 625 nm/660 hp acquisition channel and HSV-2 DNA was not detectable with the HSV-1 probe in the 470 nm/510 nm acquisition channel.

TABLE II

Bacterial, viral, and fungal pathogens for which the specificity of the HSV primers and probes were assessed.

Bacteria:

*Anaplasma phagocytophilum* (VR-1455)[1]
*Babesia microti* (30222)
*Bacteroides fragilis* (23745)
*Bartonella bacilliformis* (35685)
*Bartonella henselae* (49882)
*Bartonella quintana* (51694)
*Borrelia burgdorferi* (35210)
*Brucella ovis* (25840)
*Chlamydia pneumoniae* (VR-1356)
*Chlamydia trachomatis* (VR-901B)
*Gardnerella vaginalis* (14018)
*Helicobacter pylori* (43579)
*Mobiluncus curtisii* (35241)
*Mobiluncus mulieris* (35243)
*Mycoplasma fermentans* (15474)
*Mycoplasma genitalium* (49857)
*Mycoplasma hominis* (14027)
*Mycoplasma pneumoniae* (15377)
*Neisseria gonorrhoeae* (27628)
*Trichomonas vaginalis* (30246)
*Ureaplasma urealyticum* (27618)

Viruses:

Adenovirus (VR-1)
Cytomegalovirus (CMV; VR-807)
Coxsackie Virus (VR-184)
Epstein-Barr Virus (EBV; CCL-86)
HHV-6 (VR-1467)
HHV-8 (CRL-2230)
HPV-16 (CRL-1550)
HTLV-I (CRL-8294)
Varicella-zoster virus (VZV, VR-795)

Fungi:

*Aspergillus fumigatus* (14110)
*Candida albicans* (11651)
*Candida glabrata* (32312)
*Candida parapsilosis* (10265)
*Candida tropicalis* (10610)
*Cryptococcus neoformans* (2344)
*Trichosporan cutaneum* (4151)

[1]The ATCC catalogue designation is listed in parentheses after each organism.

Interference Analysis

To verify that components of a cervicovaginal swab DNA extraction do not inhibit or decrease the efficiency of the real-time PCR reaction, 0.5 μg of two HSV-negative DNA extracts were separately incubated in the presence of decreasing concentrations of the plasmid positive control from $10^9$ through 10 copies/reaction. In this range, no significant difference in $C_T$ score was apparent between the presence or absence of DNA extracted from cervicovaginal swab specimens.

Pyrosequencing Analysis

A Pyrosequencing procedure was adopted for two independent PCR reactions which utilized forward and reverse orientation primers capable of amplifying both HSV-1 and HSV-2 DNA. The nucleotide sequence of the regions between these primers were identified by Pyrosequencing to classify each amplicon as either HSV-1 or HSV-2. By using the Pyrosequencing data as a standard, sensitivity and specificity scores of 100.0% were calculated for both the HSV-1 and HSV-2 probes (Table III).

From the analysis of the positive HSV specimens in our laboratory, 133/479 (27.8%, 95% CI, 24.0-32.0%) and 346/479 (72.2%, 95% CI, 68.0-76.2%) were infected with HSV-1 and HSV-2, respectively. The mean age of those infected with HSV-1 was 29.5±13.5 compared with 35.6±13.9 for HSV-2 infections. A chi-square analysis did not identify a significant

TABLE III

Specificity and sensitivity calculations for the real-time HSV-1 and HSV-2 probe reactions.

(A) HSV-1

| HSV-1 Real-time PCR Result | No. of samples with the following Pyrosequencing result: | | |
|---|---|---|---|
| | Positive (HSV-1) | Negative | Total |
| Positive | 19 | 0 | 19 |
| Negative | 0 | 100 | 100 |
| Total | 19 | 100 | 119 |

(B) HSV-2

| HSV-2 Real-time PCR Result | No. of samples with the following Pyrosequencing result: | | |
|---|---|---|---|
| | Positive (HSV-2) | Negative | Total |
| Positive | 42 | 0 | 42 |
| Negative | 0 | 78 | 78 |
| Total | 42 | 78 | 120 |

(C) Summary of Results

| | Sensitivity | Specificity | Agreement |
|---|---|---|---|
| HSV-1 | 100% (19/19) | 100% (100/100) | 100% (119/119) |
| HSV-2 | 100% (42/42) | 100% (78/78) | 100% (120/120) |

Two sets of amplification primers (Table I) were selected for Pyrosequencing analysis to reduce the possibility of false negative results, which could be inherent to utilizing one non-characterized primer pair for molecular amplification.

Clinical application of the HSV-1/HSV-2 real-time PCR assay difference between the HSV-1 and HSV-2 positivity rate of those states in which over 130 specimens were collected and analyzed (p=0.112).

The present invention includes, but is not limited to, PCR methods as well as primers and probes for detecting and

TABLE IV

Population statistics and HSV positivity rate for cervicovaginal specimens tested.

| | Population | HSV-1 or HSV-2 | HSV-1 | HSV-2 |
|---|---|---|---|---|
| State | | | | |
| Texas | 1965 (42.3%)[a] | 211 (10.7%)[b] | 61 (3.1%)[b] | 150 (7.6%)[b] |
| New Jersey | 956 (20.9%) | 90 (9.4%) | 33 (3.5%) | 56 (5.9%) |
| Florida | 803 (17.5%) | 96 (12.0%) | 21 (2.6%) | 75 (9.3%) |
| Pennsylvania | 171 (3.7%) | 17 (9.9%) | 4 (2.3%) | 13 (7.6%) |
| Georgia | 149 (3.2%) | 24 (16.1%) | 2 (1.3%) | 22 (14.8%) |
| Other | 184 (4.0%) | 24 (13.0%) | 7 (3.8%) | 17 (9.2%) |
| Total | 4581 | 479 (10.5%) | 133 (2.9%) | 345 (7.5%) |
| Age | | | | |
| 0-10 | 30 | 1 (3.3%) | 1 (3.3%) | 0 (0.0%) |
| 11-20 | 674 | 74 (11.0%) | 34 (5.0%) | 40 (5.9%) |
| 21-30 | 1615 | 162 (10.0%) | 51 (3.2%) | 111 (6.9%) |
| 31-40 | 1099 | 109 (9.9%) | 23 (2.1%) | 86 (7.8%) |
| 41-50 | 639 | 67 (10.5%) | 14 (2.2%) | 53 (8.3%) |
| 51-60 | 319 | 43 (13.5%) | 7 (2.2%) | 36 (11.3%) |
| 61-70 | 126 | 15 (11.9%) | 1 (0.8%) | 14 (11.1%) |
| 71-80 | 60 | 4 (6.7%) | 1 (1.7%) | 3 (5.0%) |
| 81-90 | 17 | 3 (17.6%) | 2 (11.8%) | 1 (5.9%) |
| 91-100 | 2 | 1 (50.0%) | 0 (0.0%) | 1 (50.0%) |

[a] = Percent of the total population.
[b] = Percent positive in this category (state or age).

specifically identifying and discriminating the presence of HSV-1 and HSV-2 in a sample in a single tube reaction, for example.

Examples of this type are disclosed herein wherein the first amplicon and the second amplicon contain at least a segment of the open reading frame of the gene encoding glycoprotein B. The forward primer may comprise, for example, the nucleotide sequence: 5'-ttctgcagctcgcaccac-3' (SEQ ID NO:5). An example forward primer consists of SEQ ID NO:5. The reverse primer may comprise, for example, the nucleotide sequence: 5'-ggagcgcatcaagaccacc-3' (SEQ ID NO:6). An example reverse primer consists of SEQ ID NO:6.

Exemplary methods disclosed herein are wherein the first probe is a nucleic acid molecule capable of hybridizing to one of the strands of the first amplicon, and wherein the second probe is a nucleic acid molecule capable of hybridizing to one of the strands of the second amplicon. With regard to HSV-1 and HSV-2, for example, the first probe may comprise, for example, the nucleotide sequence: 5'-cgatggcaacgcggcccaa-catatcgttgac-3' (SEQ ID NO:7). An example first probe consists of SEQ ID NO:7. The second probe may comprise, for example, the nucleotide sequence: 5'-cgatgcgccccagcatgtcgt-tcacgt-3' (SEQ ID NO:8). An example second probe consists of SEQ ID NO:8.

Methods of the present invention further comprise, for example, determining the nucleotide sequence of at least a segment of (1) the first amplicon if the first amplicon is produced in (b), and (2) the second amplicon if the second amplicon is produced in (b).

An example method for ascertaining whether a sample includes a first strain of a herpesvirus or a second strain of a herpesvirus, comprises (a) providing (1) a nucleic acid from the sample, (2) a forward primer, and (3) a reverse primer, wherein a combination comprising the forward primer and the reverse primer is capable of amplifying, by the polymerase chain reaction, a segment of the genome of (1) the first strain to produce a first amplicon, and (2) the second strain to produce a second amplicon, and wherein the nucleotide sequence of the first amplicon and the nucleotide sequence of the second amplicon are not identical, (b) incubating a combination comprising the nucleic acid from the sample, the forward primer, and the reverse primer under conditions allowing production of (1) the first amplicon if the sample contains the first strain, and (2) the second amplicon if the sample contains the second strain, and (c) ascertaining that (1) the sample does not contain the first strain or the second strain if the first amplicon and the second amplicon are not produced in (b), (2) the sample contains the first strain and does not contain the second strain if the first amplicon is produced in (b) and the second amplicon is not produced in (b), (3) the sample does not contain the first strain and does contain the second strain if the first amplicon is not produced in (b) and the second amplicon is produced in (b), or (4) the sample contains the first strain and the second strain if the first amplicon and the second amplicon are produced in (b).

In exemplary methods disclosed herein, (a) further comprises providing a first probe specific to the first strain, and (c) further comprises determining that the first amplicon is produced in (b) if a first signal generated from the first probe is detected.

Furthermore, in exemplary methods disclosed herein, (a) further comprises providing a second probe specific to the second strain, and wherein (c) further comprises determining that the second amplicon is produced in (b) if a second signal generated from the second probe is detected.

Moreover, in exemplary methods disclosed herein, (a) further comprises providing (1) a first probe specific to the first strain, and (2) a second probe specific to the second strain, and wherein (c) further comprises determining that (1) the first amplicon is produced in (b) if a first signal generated from the first probe is detected, and (2) the second amplicon is produced in (b) if a second signal generated from the second probe is detected.

Additionally, in exemplary methods disclosed herein, the combination of (b) further comprises the first probe and the second probe, and wherein a single vessel contains the combination of (b).

Methods of the present invention are particularly described wherein the first strain of the herpesvirus is HSV-1, and wherein the second strain of the herpesvirus is HSV-2. Methods are exemplified wherein the first amplicon and the second amplicon contain at least a segment of the open reading frame of the gene encoding glycoprotein B; wherein the forward primer comprises the nucleotide sequence: 5'-ttctgcagctcg-caccac-3' (SEQ ID NO:5); wherein the forward primer consists of SEQ ID NO:5; wherein the reverse primer comprises the nucleotide sequence: 5'-ggagcgcatcaagaccacc-3' (SEQ ID NO:6); wherein the reverse primer consists of SEQ ID NO:6.

Methods are preferred wherein the first probe is a nucleic acid molecule capable of hybridizing to one of the strands of the first amplicon and wherein the second probe is a nucleic acid molecule capable of hybridizing to one of the strands of the second amplicon.

Methods of the present invention may be employed wherein the first probe comprises the nucleotide sequence 5'-cgatggcaacgcggcccaacatatcgttgac-3' (SEQ ID NO:7), for example, wherein the first probe consists of SEQ ID NO:7.

Methods of the present invention may be employed wherein the second probe comprises the nucleotide sequence: 5'-cgatgcgccccagcatgtcgttcacgt-3' (SEQ ID NO:8), for example, wherein the second probe consists of the sequence: 5'-cgatggcaacgcggcccaacatatcgttgac-3' (SEQ ID NO:7). The second probe may, for example, consists of the nucleotide sequence: 5'-cgatgcgccccagcatgtcgttcacgt-3' (SEQ ID NO:8).

Methods of the present invention encompass, for example, wherein (c), supra, further comprises determining the nucleotide sequence, e.g., by means of Pyrosequencing, at least a segment of (1) the first amplicon if the first amplicon is produced in (b), and (2) the second amplicon if the second amplicon is produced in (b).

Related Methods and Compositions

Subject matter of the present invention disclosed herein, for example, is an isolated composition for the detection and distinct identification of HSV-1 and HSV-2 comprising a first oligonucleotide primer, at least 8 nucleotides in length, common to a region within positions 978 to 1149 (5-3') of SEQ ID NO:2 and the corresponding homolog region of SEQ ID NO:1, and a second oligonucleotide primer, at least 8 nucleotides in length, that is common to a region within positions 1348 to 1546 (5-3') of SEQ ID NO:3 and the corresponding homolog region of SEQ ID NO:4. Compositions are preferred wherein at least one of the oligonucleotide primers is at least 10 nucleotides in length. Compositions of the present invention are preferred wherein one of the oligonucleotide primers is at least 10 nucleotides in length and one of the oligonucleotide primers is at least 12 nucleotides in length. Compositions of the present invention are preferred wherein each of the oligonucleotide primers is at least 12 nucleotides in length. An exemplary composition of the present invention is wherein the first oligonucleotide primer is common to a region within positions 1002 to 1149 (5-3') of SEQ ID NO:2 and the corresponding homolog region of SEQ ID NO:1. Each oligonucleotide primer which comprises a species of sequence specified in a Markush group herein, e.g., examples specified in each 'Markush group' infra, is contemplated independently. Preferred examples, for example, are wherein the first oligonucleotide primer comprises a sequence selected from the group consisting of (5-3') positions 1002-1010, 1003-1011, 1004-1012, 1005-1013, 1006-1014, 1007-1015, 1008-1016, 1009-1017, 1010-1018, 1011-1019, 1012-1020; 1013-1021, 1014-1022, 1015-1023, and 1016-1024 of SEQ ID NO:2 (each sequence is independently contemplated as is each species sequence recited herein). Preferred alternate examples are wherein the first oligonucleotide primer comprises a sequence selected from the group consisting of (5-3') positions 1041-1049, 1042-1050, 1043-1051, 1044-1052, 1045-1053, 1046-1054, 1047-1055, 1048-1056, 1049-1057, 1050-1058, 1051-1059, and 1052-1060 of SEQ ID NO:2. Further preferred alternate examples are wherein the first oligonucleotide primer comprises a sequence selected from the group consisting of (5-3') positions 1071-1079, 1072-1080, 1073-1081, 1074-1082, 1075-1083, 1076-1084, 1077-1085, 1078-1086, 1079-1087, 1080-1088, 1081-1089, and 1082-1090 of SEQ ID NO:2. Preferred examples are wherein the first oligonucleotide primer comprises a sequence selected from the group consisting of (5-3') positions 1092-1100, 1093-1101, 1094-1102, 1095-1103, 1096-1104, 1097-1105, 1098-1106, 1099-1107, 1100-1108, 1101-1109, 1102-1110, and 1103-1111 of SEQ ID NO:2. Preferred alternate examples are wherein the first oligonucleotide primer comprises a sequence selected from the group consisting of (5-3') positions 1113-1121, 1114-1122, 1115-1123, 1116-1124, 1117-1125, 1118-1126, and 1119-1127 of SEQ ID NO:2.

An exemplary composition of the present invention is wherein the first oligonucleotide primer is common to a region within positions 1002 to 1149 (5-3') of SEQ ID NO:2 and the corresponding homolog region of SEQ ID NO:1.

Compositions described herein are preferred wherein the first oligonucleotide primer is common to a region within positions 1002 to 1149 (5-3') of SEQ ID NO:2 and the corresponding homolog region of SEQ ID NO:1, for example, wherein the first oligonucleotide primer is common to a region within positions 1128 to 1149 (5-3') of SEQ ID NO:2. Isolated composition for the detection and distinct identification of HSV-1 and HSV-2 are preferred wherein the first oligonucleotide primer comprises a sequence selected from the group consisting of (5-3') positions 1128-1136, 1129-1137, 1130-1138, 1131-1139, 1132-1140, 1133-1141, 1134-1142, 1135-1143, 1136-1144, 1137-1145, 1138-1146, 1139-1147, 1140-1148, and 1141-1149 of SEQ ID NO:2.

Subject matter of the present invention disclosed herein, for example, is an isolated composition for the detection and distinct identification of HSV-1 and HSV-2 comprising: a first oligonucleotide primer, at least 8 nucleotides in length, common to a region within positions 978 to 1149 (5-3') of SEQ ID NO:2 and the corresponding homolog region of SEQ ID NO:1, and a second oligonucleotide primer, at least 8 nucleotides in length, that is common to a region within positions 1348 to 1546 (5-3') of SEQ ID NO:3 and the corresponding homolog region of SEQ ID NO:4. Compositions are preferred wherein the second oligonucleotide primer is common to a region within positions 1457 to 1546 (5-3') of SEQ ID NO:4 and the corresponding homolog region of SEQ ID NO:3.

Preferred examples are wherein the second oligonucleotide primer comprises a sequence selected from the group consisting of (5-3') positions 1538 to 1546, 1537 to 1545, 1536 to 1544, 1535 to 1543, 1534 to 1542, and 1533 to 1541 of SEQ ID NO:4. Alternate preferred examples are wherein the second oligonucleotide primer comprises a sequence selected from the group consisting of (5-3') positions 1521-1529, 1520-1528, 1519-1527, 1518-1526, 1517-1525, 1516-1524, and 1515-1523 of SEQ ID NO:4. Alternate preferred examples are wherein the second oligonucleotide primer comprises a sequence selected from the group consisting of (5-3') positions 1504-1512, 1503-1511, 1502-1510, and 1501-1509 of SEQ ID NO:4. Alternate preferred examples are wherein the second oligonucleotide primer comprises a sequence selected from the group consisting of (5-3') positions 1491-1499, 1490-1498, 1489-1497, 1488-1496, 1487-1495, 1486-1494, 1485-1493, 1484-1492, 1483-1491, 1482-1490, 1481-1489, 1480-1488, 1479-1487, 1478-1486, 1477-1485, 1476-1484, 1475-1483, 1474-1482, 1473-1481, 1472-1480, 1471-1479, 1470-1478, 1469-1477, 1468-1476, 1467-1475, 1466-1474, 1465-1473, 1464-1472, 1463-1471, 1462-1470, 1461-1469, 1460-1468, 1459-1467, and 1458-1466 of SEQ ID NO:4.

Further compositions of the present invention for the detection and distinct identification of HSV-1 and HSV-2 which comprise a first oligonucleotide primer, at least 8 nucleotides in length, common to a region within positions 978 to 1149 (5-3') of SEQ ID NO:2 and the corresponding homolog region of SEQ ID NO:1, and a second oligonucleotide primer, at least 8 nucleotides in length, that is common to a region within positions 1348 to 1546 (5-3') of SEQ ID NO:3 and the corresponding homolog region of SEQ ID NO:4, further comprise a first oligonucleotide probe between about 15 and about 40 nucleotides in length specific to a sequence selected from the group consisting of SEQ ID NO:1 and SEQ ID NO:3 and a second oligonucleotide probe between about 15 and about 40 nucleotides in length specific to a sequence selected from the group consisting of SEQ ID NO:2 and SEQ ID NO:4. Compositions are preferred wherein the first probe is specific to a nucleotide sequence within positions 978 to 1384 SEQ ID NO:2 or an exact complement thereof, and the second oligonucleotide probe is specific to the corresponding homolog region of SEQ ID NO:1 or an exact complement thereof. Compositions of this type are preferred wherein the first probe is specific to a nucleotide sequence within positions 1002 to 1269 SEQ ID NO:2 or an exact complement thereof, and the second oligonucleotide probe is specific to the corresponding homolog region of SEQ ID NO:1 or an exact complement thereof. Compositions of this type are further preferred wherein the first probe is specific to a nucleotide sequence within positions 1126 to 1230 SEQ ID NO:2 or an exact complement thereof, and the second oligonucleotide probe is specific to the corresponding homolog region of SEQ ID NO:1 or an exact complement thereof. Compositions of this type are further preferred wherein the first probe is specific to a nucleotide sequence within positions 1140 to 1190 SEQ ID NO:2 or an exact complement thereof, and the second oligonucleotide probe is specific to the corresponding homolog region of SEQ ID NO:1 or an exact complement thereof.

Compositions according to the present invention are preferred wherein the first and second oligonucleotide probes are each detectably labeled with distinctly different detectable labels.

The present invention is directed toward a real-time method for detecting and identifying distinct species of nucleic acids, in a single container, from a certain genus of infectious agents comprising providing a forward PCR primer common to a homologous gene region between the distinct species, and providing a reverse PCR primer common to a homologous gene region between the distinct species, to thereby define a PCR target region amongst the species, and providing a first oligonucleotide probe specific to a nucleic acid sequence within the target region that is characteristic of a first species, providing a second oligonucleotide probe specific to a nucleic acid sequence within the target region that is characteristic of a second species, wherein the first and second oligonucleotide probes are each detectably labeled with distinctly different detectable labels, conducting a PCR reaction in the container by means of the primers to amplify the target region amongst the species, and detecting the distinct labels, thereby identifying distinct species of nucleic acids corresponding to distinct species of infectious agents. These methods of the present invention are preferred wherein the infectious agent is a member of the Herpesviridae family. Methods are preferred wherein the first oligonucleotide probe is between about 15 and about 40 nucleotides in length specific to a sequence selected from the group consisting of SEQ ID NO:1 and SEQ ID NO:3 and a second oligonucleotide probe between about 15 and about 40 nucleotides in length specific to a sequence selected from the group consisting of SEQ ID NO:2 and SEQ ID NO:4. Methods are particularly preferred wherein the genus of infectious agents is HSV-1 and HSV-2 and the forward PCR primer is common to a region within positions 978 to 1149 (5-3') of SEQ ID NO:2 and the corresponding homolog region of SEQ ID NO:1, and the reverse PCR primer is common to a region within positions 1348 to 1546 (5-3') of SEQ ID NO:4 and the corresponding homolog region of SEQ ID NO:3. A method of this type is preferred wherein the first probe is specific to a nucleotide sequence within positions 978 to 1384 SEQ ID NO:2 or an exact complement thereof, and the second oligonucleotide probe is specific to the corresponding homolog region of SEQ ID NO:1 or an exact complement thereof.

EXAMPLES

Example I

HSV-1 and HSV-2 Controls and Clinical Specimens

Confirmed HSV-1 (#VR-539) and HSV-2 (#VR-734) specimens originally isolated from a human encephalitis brain specimen and a genital infection, respectively, were purchased from the American Type Cultures Collection (ATCC, Manassas, Va.). Clinical specimens were submitted to our laboratory for HSV testing from November 2003 through January 2004 by obstetrician/gynecologist offices. Information describing the clinical presentation of the patients was not provided. Cervicovaginal sampling was performed with a Cellmatics swab (BD, Sparks, Md.) that was placed in 2 ml viral transport medium. Upon receipt to the laboratory, DNA was extracted by mixing 470 µl of the transport media with 25 µl of 10% sodium dodecyl sulfate and 12 µl of freshly prepared DNase-free 10 mg/ml proteinase-K, and incubating for 2 hours at 55° C. DNA was phenol:chloroform:isoamyl alcohol extracted and recovered by ethanol precipitation. DNA was pelleted, dried in a speed vacuum, and resuspended in 20 µl TE buffer. Absorbance was monitored by 260/280 readings with a BioPhotometer spectrophotometer (Eppendorf, Westbury, N.Y.) and the DNA concentration was adjusted to 0.2 µg/µl prior to PCR analysis.

Example II

Conventional PCR Amplification Parameters

Each 50 µl reaction contained 1 µg template DNA, 1×PCR buffer, 1.5 mM $MgCl_2$, 0.25 mM dNTP (dATP, dCTP, dGTP, and dTTP), 0.2 µM HSV2a-1, 0.2 µM HSV2a-2, and 2.5 U Taq DNA polymerase (USB, Cleveland, Ohio). Cycling conditions included an initial denaturation step of 94° C. for 3 minutes followed by 30 cycles of 94° C. for 1 min, 53° C. for 1 min, and 72° C. for 1 min in a T3 Thermocycler (Biometra, Gottingen, Germany). A 10 min extension step at 72° C. concluded each reaction. PCR products were resolved through a 2% agarose gel containing 0.5 µg/ml ethidium bromide and visualized with a SynGene Gel Documentation System (Frederick, Md.). The amplification target of the reaction was the HSV glycoprotein B gene and resulted in a 342 by fragment; both HSV-1 and HSV-2 are amplified with this primer pair combination (Cone et al., 1991, J. Infect. Dis. 164(4):757-60.).

Example III

Preparation of HSV-1 and HSV-2 Vector Controls. Positive controls for each probe were generated by subcloning amplicons derived from using forward and reverse orientation amplification primers and template DNA extracted from HSV-1 and HSV-2 ATCC-purchased controls. Amplicons were subcloned into the pCRII-TOPO vector of the TOPO TA Cloning Dual Promoter kit (Invitrogen, Carlsbad, Calif.) according to the manufacturer's instructions. The correct constructs were identified by colony PCR and restriction digestion by standard molecular biology procedures (Ausubel et al., 1997, Nucleic Acids Res. 25(17):3389-402.). Large-scale plasmid preparations for each were prepared with the Qiagen plasmid extraction kit and quantitated.

All publications and patents referred to herein are incorporated by reference. Various modifications and variations of the described subject matter will be apparent to those skilled in the art without departing from the scope and spirit of the invention. Although the invention has been described in connection with specific embodiments, it should be understood that the invention as claimed should not be unduly limited to these embodiments. Indeed, various modifications for carrying out the invention are obvious to those skilled in the art and are intended to be within the scope of the following claims.

What is claimed is:

1. A method for ascertaining whether a sample includes a first strain of a herpes virus or a second strain of a herpes virus, the method comprising the steps of:
   (a) providing a single vessel wherein said vessel comprises a reaction mixture consisting of (1) a nucleic acid from the sample, (2) a forward primer, (3) a reverse primer, (4) a first probe specific to the first strain, and (5) a second probe specific to the second strain,
   wherein the forward primer and the reverse primer are capable of acting together as a primer pair in the amplification, by the polymerase chain reaction, of a segment of the genome of both (1) the first strain to produce a first amplicon, and (2) the second strain to produce a second amplicon, and
   wherein the nucleotide sequence of the first amplicon and the nucleotide sequence of the second amplicon are not identical;
   (b) incubating the vessel under conditions allowing production of (1) the first amplicon if the sample contains the first strain, and (2) the second amplicon if the sample contains the second strain; and
   (c) detecting a first signal generated from the first probe if the first amplicon is produced in (b), and detecting a second signal generated from the second probe if the second amplicon is produced in (b),
   wherein the first strain is HSV-1 and the second strain is HSV-2, and the first amplicon and the second amplicon contain a segment of the open reading frame of a gene encoding glycoprotein B.

2. The method of claim 1, wherein the forward primer consists of the following nucleotide sequence: 5'-ttctgcagctcgcaccac-3' (SEQ ID NO:5).

3. The method of claim 1, wherein the reverse primer consists of the following nucleotide sequence: 5'-ggagcgcatcaagaccacc-3' (SEQ ID NO:6).

4. The method of claim 1, wherein the first probe is a nucleic acid molecule capable of hybridizing to one of the strands of the first amplicon, and wherein the second probe is a nucleic acid molecule capable of hybridizing to one of the strands of the second amplicon.

5. The method of claim 1, wherein the first probe consists of the following nucleotide sequence: 5'-cgatggcaacgcggcccaacatatcgttgac-3' (SEQ ID NO:7).

6. The method of claim 1, wherein the second probe consists of the following nucleotide sequence: 5'-cgatgcgccccagcatgtcgttcacgt-3' (SEQ ID NO:8).

7. The method of claim 1, further comprising determining the nucleotide sequence of at least a segment of (1) the first amplicon if the first amplicon is produced in (b), and (2) the second amplicon if the second amplicon is produced in (b).

8. The method of claim 1, further comprising the step of ascertaining that (1) the sample does not contain the first strain or the second strain if the first signal and the second signal are not detected in (c), (2) the sample contains the first strain and does not contain the second strain if the first signal, is detected in (c) and the second signal is not detected in (c), (3) the sample does not contain the first strain and contains the second strain if the first signal is not detected in (c) and the second signal is detected in (c), or (4) the sample contains the first strain and the second strain if the first signal and the second signal are detected in (c).

9. The method of claim 1, wherein the polymerase chain reaction is a real-time polymerase chain reaction.

10. The method of claim 1, wherein the polymerase chain reaction is a real-time polymerase chain reaction with a sensitivity of 100% and a specificity of 100%.

* * * * *

SEQUENCE LISTING

```
<160> NUMBER OF SEQ ID NOS: 12

<210> SEQ ID NO 1
<211> LENGTH: 2716
<212> TYPE: DNA
<213> ORGANISM: herpes simplex virus type 1

<400> SEQUENCE: 1
atcacaggtc gtcctcgtcg gcgtcaccgt ctttgttggg aacttgggtg tagttggtgt      60
```

```
tgcggcgctt gcgcatgacc atgtcggtga ccttggcgct gagcagcgcg ctcgtgccct    120
tcttcttggc cttgtgttcc gtgcgctcca tggcagacac cagggccatg taccgtatca    180
tctcccgggc ctcggctagc ttggcctcgt caaagtcgcc gccctcctcg ccctccccgg    240
acgcgtccgg gttggtgggg ttcttgagct ccttggtggt tagcgggtac agggccttca    300
tggggttgct ctgcagccgc atgacgtagc gaaaggcgaa gaaggccgcc gccaggccgg    360
ccaggaccaa cagacccacg gccagcgccc aaaggggtt ggacatgaag gaggacacgc    420
ccgacacggc cgataccacg ccgcccacga tgcccatcac caccttgccg accgcgcgcc    480
ccaggtcgcc catcccctcg aagaacgcgc ccaggcccgc aaacatggcg gcgttggcgt    540
cggcgtggat gaccgtgtcg atgtcggcga agcgcaggtc gtgcagctgg ttgcggcgct    600
ggacctccgt gtagtccagc aggccgctgt ccttgatctc gtggcgggtg tacacctcca    660
gggggacaaa ctcgtgatcc tccagcatgg tgatgttgag gtcgatgaag gtgctgacgg    720
tggtgatgtc ggcgcggctc agctggtggg agtacgcgta ctcctcgaag tacacgtagc    780
ccccaccgaa ggtgaagtag cgccggtgtc ccacggtgca cggctcgatc gcatcgcgcg    840
tcagccgcag ctcgttgttc tccccagct gcccctcgac caacgggccc tggtcttcgt    900
accgaaagct gaccaggggg cggctgtagc aggccccggg ccgcgagctg atgcgcatcg    960
agttttggac gatcacgttg tccgcggcga ccggcacgca cgtggagacg ccatcacgt    1020 cgccgagcat ccgcgcgctc acccgccggc ccacggtggc cgaggcgatg gcgttgggt    1080 tcagcttgcg ggcctcgttc acagggtca gctcgtgatt ctgcagctcg caccacgcga    1140
tggcaacgcg gcccaacata tcgttgacat ggcgctgtat gtggttgtac gtaaactgca    1200
gcctggcgaa ctcgatggag gaggtggtct tgatgcgctc cacggacgcg ttggcgctgg    1260
ccccgggcgg cggggggcgtg gggtttggg gcttgcggct ctgctcgcgg aggtgttccc    1320
gcacgtacag ctccgcgagc gtgttgctga aaggggctg gtacgcgatc agaaagcccc    1380
cattggccag gtagtactgc ggctggccca ccttgatgtg cgtcgcgttg tacctgcggg    1440
cgaagatgcg gtccatggcg tcgcgggcgt ccttgccgat gcagtccccc aggtccacgc    1500
gcgagagcgg gtactcggtc aggttggtgg tgaaggtggt ggatatggcg tcggaagaga    1560
atcggaagga ccgccgtac tcggagcgca gcatctcgtc cacctcctgc cacttggtca    1620
tggtgcagac cgacgggcgc tttggcaccc agtcccaggc cacggtgaac ttgggggtcg    1680
tgagcaggtt ccgggtggtc ggcgccgtgg cccgggcctt ggtggtgagg tcgcgcgcgt    1740
agaagccgtc gacctgcttg aagcggtcgg cggcgtagct ggtgtgttcg gtgtgcgacc    1800
cctcccggta gccgtaaaac ggggacatgt acacaaagtc gccagtcgcc aacacaaact    1860
cgtcgtacgg gtacaccgag cgcgcgtcca cctcctcgac gatgcagttt accgtcgtcc    1920
cgtaccggtg gaacgcctcc acccgcgagg ggttgtactt gaggtcggtg gtgtgccagc    1980
cccggctcgt gcgggtcgcg gcgttggccg gtttcagctc catgtcggtc tcgtggtcgt    2040
cccggtgaaa cgcggtggtc tccaggttgt tgcgcacgta cttggccgtg gaccgacaga    2100 ccccccttggc gttgatcttg tcgatcacct cctcgaaggg gacgggggcg cggtcctcaa    2160
agatccccat aaactgggag tagcggtggc cgaaccacac ctgcgaaacg tgacgtctt    2220 tgtagtacat ggtggccttg aacttgtacg gggcgatgtt ctccttgaag accaccgcga    2280
tgccctccgt gtagttctga ccctcgggcc gggtcgggca gcggcgcggc tgctcgaact    2340
gcaccaccgt ggcgcccgtg gggggtgggc acacgtaaaa gtttgcatcg gtgttctccg    2400
ccttgatgtc ccgcaggtgc tcgcgcaggg tggcgtggcc cgcggcgacg gtcgcgttgt    2460
```

-continued

```
cgccggcggg gcgcggcggc tttgggggtt tcggttttct gttcttcttc ggtttcgggt      2520
cccccgttgg gggggcgcca ggggcgggcg gcgccggagt ggcagggccc ccgttcgccg      2580
cctgggtcgc ggccgcgacc ccaggcgtgc cgggggaact cggagccgcc gacgccacca      2640 ggaccccag cgtcaacccc aagagcgccc atacgacgaa ccaccggcgc ccccgcgcgg       2700
gggcgccctg gcgcat                                                      2716

<210> SEQ ID NO 2
<211> LENGTH: 2716
<212> TYPE: DNA
<213> ORGANISM: herpes simplex virus type 2

<400> SEQUENCE: 2
cttagagctc gtcttcgtct ccggcctcgt cctcgttgtg gagcggagag tacctggctt        60
tgttgcgctt gcgcagaacc atgttggtga ccttggagct gagcagggcg ctcgtgccct       120
tctttctggc cttgtgttcc gtgcgctcca tggccgacac caaagccata tatcggatca      180
tttctcgggc ctcggccaac ttggcctcgt caaacccgcc cccctccgcg ccttcctccc       240 cctcccccgcc cacgccccg gggtcggaag tcttgagttc cttggtggtg agcggataca       300
gggccttcat gggattgcgt tgcagttgca ggacgtagcg gaaggcgaag aaggccgcga       360
ccaggccggc caggaccagc agccccacgg caagcgcccc gaaggggttg gacataaagg       420
aggacacgcc cgagacggcc gacaccacgc cccccactac tcccatgact accttgccga       480
ccgcgcgccc caagtccccc atccctcga agaacgcgca cagccccgcg aacatggcgg       540
cgttggcgtc ggcgcggatg accgtgtcga tgtcggcaaa gcgcaggtcg tgcagctggt       600
tgcggcgctg gacctccgtg tagtccagca ggccgctgtc cttgatctcg tggcgcgtgt      660
agacctccag gggcacaaac tcgtggtcct ccagcatggt gatgttcagg tcgatgaagg       720
tgctgacggt ggtgacgtcg gcgcgactca gctggtgaga gtacgcgtac tcctcgaagt       780
acacgtagcc cccgccgaag atgaagtagc gccggtggcc cacggtgcac ggctcgagcg       840
cgtcgcgggt gaggcgcagc tcgttgttct cgcccagctg cccctcgatc agcgggccct       900
ggtcttcgta ccgaaagctg accagggggc ggctgtagca cgtccccggc cgcgagctga       960
cgcgcatcga gttctgcacg atcacgttgt ccggggcgac gggcacgcac gtggagacgg      1020
ccatgacgtc tccgagcatg cgcgcgctca cccgccggcc gacggtggcg gaggcgatgg      1080 cgttgggggtt gagcttgcgg gcctcgttcc agagagtcag ctcgtggttc tgcagctcgc      1140
accacgcgac ggcgatgcgc cccagcatgt cattcacgtg cgctgtatg tggttatacg       1200 taaactgcag ccgggcgaac tcgatcgagg aggtggtctt gatgcgctcc acggacgcgt       1260
tggcgctggg cgcctcccgc agtggcgcgg cgtggcatt ccggggcttg cggtcctgct       1320
cccgcatgta ctcccgcacg tacagctcgg cgagcgtgtt gctgaggagg ggctggtacg      1380
cgatgaggaa gccccccgtg gccaggtagt actgcggctg gcccaccttg atgtgcgtgg      1440
cgttgtactt gcgcgcaaac atgcggtcga tggcctcgcg ggcatcccgg ccgatgcagt       1500
cgcccaggtc gacgcgcgag agcgagtact cggtcaggtt ggtggtgaag gtggtcgaga      1560
tggcgtcgga ggagaagcgg aaggagccgc cgtactcggc gcggagcatc tcgtccacct      1620
cctgccactt ggtcatggtg cagaccgccg gtcgcttcgg cacccagtcc caggccacgg      1680
taaacttggg ggtcgtcagc aagttgcggg tcgtcggcga cgtggcccgg gccttcgtgg       1740
tgaggtcgcg cgcgtagaag ccgtcgacct gcttgaagcg gtcggcggcg tagctggtgt      1800
gctcggtgtg cgaccccctcc cggtagccgt aaaacgggga catgtacaca aagtcgcccg      1860
```

-continued

| | |
|---|---|
| tcgccagcac aaactcatcg tacgggtaca ccgaccgcgc gtccacctcc tcgacgatgc | 1920 |
| agttgaccgt cgtgccgtac cgatggaacg cctccacccg cgaggggttg tacttgaggt | 1980 |
| cggtggtgtg ccaccccgg ctcgtgcgcg tggcgacctt cgccggcttg agctccatgt | 2040 |
| cggtctcgtg gtcgtcccgg tgaaacgcgg tggtctccat gttgttccgc acgtacttgg | 2100 |
| ccgtggagcg gcagaccccc ttggtgttaa tcttgtcgat cacctcctcg aagggaacgg | 2160 |
| gggcgcggtc ctcgaatatc cccataaact gggagtagcg gtggccgaac cacacctgcg | 2220 |
| acacggtcac gtctttgtag tacatggtgg ccttgaattt gtacgggcg atgttctcct | 2280 |
| tgaagaccac cgcgatgccc tccgtgtagt tctgccccctc cgggcgcgtc gggcagcggc | 2340 |
| gcggctgctc aaactgcacc accgtggcgc ccgtcggggg cggcacacg taaaactggg | 2400 |
| catcggcgtt ctcgaccttg atttcccgca ggtgcgcgcg cagcgtggcg tggccggcgg | 2460 |
| cgacggtcgc gttggcgtcg gggggcgggg tcgcctcggg ccgcttgggc ggcttttttgg | 2520 |
| ttttccgctt ccgggccttg gtggtcgcgg ggctcgggac ggggggcggc cgggaggcgg | 2580 |
| gaccccgtt cgccgcgacg gtcgcggcca cgccgcccga ggcgcggggg gccgccgggg | 2640 |
| ccgccggggc cgccgacgcc accgcggcca ccagcgcccc cacgaccagc gcgcaaatca | 2700 |
| agcccccccc gcgcat | 2716 |

<210> SEQ ID NO 3
<211> LENGTH: 2716
<212> TYPE: DNA
<213> ORGANISM: herpes simplex virus type 1

<400> SEQUENCE: 3

| | |
|---|---|
| atgcgccagg gcgcccccgc gcggggggcgc cggtggttcg tcgtatgggc gctcttgggg | 60 |
| ttgacgctgg gggtcctggt ggcgtcggcg gctccgagtt cccccggcac gcctggggtc | 120 |
| gcggccgcga cccaggcggc gaacgggggc cctgccactc cggcgccgcc cgcccctggc | 180 |
| gccccccaa cggggaccc gaaaccgaag aagaacagaa aaccgaaacc cccaaagccg | 240 |
| ccgcgcccg ccggcgacaa cgcgaccgtc gccgcgggcc acgccaccct gcgcgagcac | 300 |
| ctgcgggaca tcaaggcgga gaacaccgat gcaaactttt acgtgtgccc accccccacg | 360 |
| ggcgccacgg tggtgcagtt cgagcagccg cgccgctgcc cgaccccggcc cgagggtcag | 420 |
| aactacacgg agggcatcgc ggtggtcttc aaggagaaca tcgccccgta caagttcaag | 480 |
| gccaccatgt actacaaaga cgtcaccgtt tcgcaggtgt ggttcggcca ccgctactcc | 540 |
| cagtttatgg ggatctttga ggaccgcgcc cccgtcccct tcgaggaggt gatcgacaag | 600 |
| atcaacgcca aggggtctg tcggtccacg gccaagtacg tgcgcaacaa cctggagacc | 660 |
| accgcgtttc accgggacga ccacgagacc gacatggagc tgaaaccggc caacgccgcg | 720 |
| acccgcacga gccggggctg gcacaccacc gacctcaagt acaacccctc gcgggtggag | 780 |
| gcgttccacc ggtacgggac gacggtaaac tgcatcgtcg aggaggtgga cgcgcgctcg | 840 |
| gtgtacccgt acgacgagtt tgtgttggcg actggcgact ttgtgtacat gtccccgttt | 900 |
| tacggctacc gggaggggtc gcacaccgaa cacaccagct acgccgccga ccgcttcaag | 960 |
| caggtcgacg gcttctacgc gcgcgacctc accaccaagg cccgggccac ggcgccgacc | 1020 |
| acccggaacc tgctcacgac ccccaagttc accgtgccct gggactgggt gccaaagcgc | 1080 |
| ccgtcggtct gcaccatgac caagtggcag gaggtggacg agatgctgcg ctccgagtac | 1140 |
| ggcggctcct ccgattctc ttccgacgcc atatccacca ccttcaccac caacctgacc | 1200 |
| gagtacccgc tctcgcgcgt ggacctgggg gactgcatcg gcaaggacgc ccgcgacgcc | 1260 |

| | |
|---|---:|
| atggaccgca tcttcgcccg caggtacaac gcgacgcaca tcaaggtggg ccagccgcag | 1320 |
| tactacctgg ccaatggggg ctttctgatc gcgtaccagc cccttctcag caacacgctc | 1380 |
| gcggagctgt acgtgcggga acacctccgc gagcagagcc gcaagccccc aaaccccacg | 1440 |
| cccccgccgc ccggggccag cgccaacgcg tccgtggagc gcatcaagac cacctcctcc | 1500 |
| atcgagttcg ccaggctgca gtttacgtac aaccacatac agcgccatgt caacgatatg | 1560 |
| ttgggccgcg ttgccatcgc gtggtgcgag ctgcagaatc acgagctgac cctgtggaac | 1620 |
| gaggcccgca agctgaaccc caacgccatc gcctcggcca ccgtgggccg cgggtgagc | 1680 |
| gcgcggatgc tcgcgacgt gatggccgtc tccacgtgcg tgccggtcgc cgcggacaac | 1740 |
| gtgatcgtcc aaaactcgat gcgcatcagc tcgcggcccg gggcctgcta cagccgcccc | 1800 |
| ctggtcagct ttcggtacga agaccagggc ccgttggtcg aggggcagct gggggagaac | 1860 |
| aacgagctgc ggctgacgcg cgatgcgatc gagccgtgca ccgtgggaca ccggcgctac | 1920 |
| ttcaccttcg gtgggggcta cgtgtacttc gaggagtacg cgtactccca ccagctgagc | 1980 |
| cgcgccgaca tcaccaccgt cagcaccttc atcgacctca acatcaccat gctggaggat | 2040 |
| cacgagtttg tccccctgga ggtgtacacc cgccacgaga tcaaggacag cggcctgctg | 2100 |
| gactacacgg aggtccagcg ccgcaaccag ctgcacgacc tgcgcttcgc cgacatcgac | 2160 |
| acggtcatcc acgccgacgc caacgccgcc atgtttgcgg gcctgggcgc gttcttcgag | 2220 |
| gggatgggcg acctggggcg cgcggtcggc aaggtggtga tgggcatcgt gggcggcgtg | 2280 |
| gtatcggccg tgtcgggcgt gtcctccttc atgtccaacc cctttggggc gctggccgtg | 2340 |
| ggtctgttgg tcctggccgg cctggcggcg gccttcttcg cctttcgcta cgtcatgcgg | 2400 |
| ctgcagagca accccatgaa ggccctgtac ccgctaacca ccaaggagct caagaacccc | 2460 |
| accaacccgg acgcgtccgg ggagggcgag gagggcggcg actttgacga ggccaagcta | 2520 |
| gccgaggccc gggagatgat acggtacatg gccctggtgt ctgccatgga gcgcacggaa | 2580 |
| cacaaggcca agaagaaggg cacgagccgc gctgctcagcg ccaaggtcac cgacatggtc | 2640 |
| atgcgcaagc gccgcaacac caactacacc caagttccca acaaagacgg tgacgccgac | 2700 |
| gaggacgacc tgtgat | 2716 |

<210> SEQ ID NO 4
<211> LENGTH: 2716
<212> TYPE: DNA
<213> ORGANISM: herpes simplex virus type 2

<400> SEQUENCE: 4

| | |
|---|---:|
| atgcgcgggg ggggcttgat ttgcgcgctg gtcgtggggg cgctggtggc cgcggtggcg | 60 |
| tcggcggccc cggcggcccc ggcggccccc gcgcctcgg gcggcgtggc cgcgaccgtc | 120 |
| gcggcgaacg ggggtcccgc ctcccggccg ccccccgtcc cgagcccgc gaccaccaag | 180 |
| gcccggaagc ggaaaaccaa aaagccgccc aagcggcccg aggcgacccc gcccccgac | 240 |
| gccaacgcga ccgtcgccgc cggccacgcc acgctgcgcg cgcacctgcg ggaaatcaag | 300 |
| gtcgagaacg ccgatgccca gttttacgtg tgcccgcccc cgacgggcgc cacggtggtg | 360 |
| cagtttgagc agccgcgccg ctgcccgacg cgcccggagg ggcagaacta cacggagggc | 420 |
| atcgcggtgt tcttcaagga gaacatcgcc ccgtacaaat tcaaggccac catgtactac | 480 |
| aaagacgtga ccgtgtcgca ggtgtggttc ggccaccgct actcccagtt tatggggata | 540 |
| ttcgaggacc gcgcccccgt tcccttcgag gaggtgatcg acaagattaa caccaagggg | 600 |
| gtctgccgct ccacggccaa gtacgtgcgg aacaacatgg agaccaccgc gtttcaccgg | 660 |

```
gacgaccacg agaccgacat ggagctcaag ccggcgaagg tcgccacgcg cacgagccgg      720
gggtggcaca ccaccgacct caagtacaac ccctcgcggg tggaggcgtt ccatcggtac      780
ggcacgacgg tcaactgcat cgtcgaggag gtggacgcgc ggtcggtgta cccgtacgat      840
gagtttgtgc tggcgacggg cgactttgtg tacatgtccc cgttttacgg ctaccgggag      900
gggtcgcaca ccgagcacac cagctacgcc gccgaccgct tcaagcaggt cgacggcttc      960
tacgcgcgcg acctcaccac gaaggccggg ccacgtcgc cgacgacccg caacttgctg     1020
acgaccccca gtttaccgt ggcctgggac tgggtgccga agcgaccggc ggtctgcacc     1080
atgaccaagt ggcaggaggt ggacgagatg ctccgcgccg agtacggcgg ctccttccgc     1140
ttctcctccg acgccatctc gaccaccttc accaccaacc tgaccgagta ctcgctctcg     1200
cgcgtcgacc tgggcgactg catcggccgg gatgcccgcg aggccatcga ccgcatgttt     1260
gcgcgcaagt acaacgccac gcacatcaag gtgggccagc cgcagtacta cctggccacg     1320
gggggcttcc tcatcgcgta ccagcccctc ctcagcaaca cgctcgccga gctgtacgtg     1380
cgggagtaca tgcgggagca ggaccgcaag ccccggaatg ccacgcccgc gccactgcgg     1440
gaggcgccca cgccaacgc gtccgtggag cgcatcaaga ccacctcctc gatcgagttc     1500
gcccggctgc agtttacgta taaccacata cagcgccacg tgaatgacat gctggggcgc     1560
atcgccgtcg cgtggtgcga gctgcagaac cacgagctga ctctctggaa cgaggcccgc     1620
aagctcaacc ccaacgccat cgcctccgcc accgtcggcc ggcgggtgag cgcgcgcatg     1680
ctcggagacg tcatggccgt ctccacgtgc gtgcccgtcg ccccggacaa cgtgatcgtg     1740
cagaactcga tgcgcgtcag ctcgcggccg gggacgtgct acagccgccc cctggtcagc     1800
tttcggtacg aagaccaggg cccgctgatc gaggggcagc tgggcgagaa caacgagctg     1860
cgcctcaccc gcgacgcgct cgagccgtgc accgtgggcc accggcgcta cttcatcttc     1920
ggcgggggct acgtgtactt cgaggagtac gcgtactctc accagctgag tcgcgccgac     1980
gtcaccaccg tcagcacctt catcgacctg aacatcacca tgctggagga ccacgagttt     2040
gtgcccctgg aggtctacac gccgccacgag atcaaggaca gcggcctgct ggactacacg     2100
gaggtccagc gccgcaacca gctgcacgac ctgcgctttg ccgacatcga cacggtcatc     2160
cgcgccgacg ccaacgccgc catgttcgcg gggctgtgcg cgttcttcga ggggatgggg     2220
gacttggggc gcgcggtcgg caaggtagtc atggagtag tggggggcgt ggtgtcggcc     2280
gtctcgggcg tgtcctcctt tatgtccaac cccttcgggg cgcttgccgt ggggctgctg     2340
gtcctggccg gcctggtcgc ggccttcttc gccttccgct acgtcctgca actgcaacgc     2400
aatcccatga aggccctgta tccgctcacc accaaggaac tcaagacttc cgaccccggg     2460
ggcgtgggcg gggaggggga ggaaggcgcg gagggggcg ggtttgacga ggccaagttg     2520
gccgaggccc gagaaatgat ccgatatatg gctttggtgt cggccatgga gcgcacggaa     2580
cacaaggcca gaaagaaggg cacgagcgcc ctgctcagct ccaaggtcac caacatggtt     2640
ctgcgcaagc gcaacaaagc caggtactct ccgctccaca acgaggacga ggccggagac     2700
gaagacgagc tctaag                                                     2716
```

<210> SEQ ID NO 5
<211> LENGTH: 18
<212> TYPE: DNA
<213> ORGANISM: herpes simplex virus

<400> SEQUENCE: 5

```
ttctgcagct cgcaccac                                                     18
```

```
<210> SEQ ID NO 6
<211> LENGTH: 19
<212> TYPE: DNA
<213> ORGANISM: herpes simplex virus

<400> SEQUENCE: 6
ggagcgcatc aagaccacc                                                19

<210> SEQ ID NO 7
<211> LENGTH: 31
<212> TYPE: DNA
<213> ORGANISM: herpes simplex virus type 1

<400> SEQUENCE: 7
cgatggcaac gcggcccaac atatcgttga c                                  31

<210> SEQ ID NO 8
<211> LENGTH: 27
<212> TYPE: DNA
<213> ORGANISM: herpes simplex virus type 2

<400> SEQUENCE: 8
cgatgcgccc cagcatgtcg ttcacgt                                       27

<210> SEQ ID NO 9
<211> LENGTH: 27
<212> TYPE: DNA
<213> ORGANISM: herpes simplex virus type 2

<400> SEQUENCE: 9
cgatgcgccc cagcatgtca ttcacgt                                       27

<210> SEQ ID NO 10
<211> LENGTH: 20
<212> TYPE: DNA
<213> ORGANISM: herpes simplex virus

<400> SEQUENCE: 10
ctggtcagct ttcggtacga                                               20

<210> SEQ ID NO 11
<211> LENGTH: 20
<212> TYPE: DNA
<213> ORGANISM: herpes simplex virus

<400> SEQUENCE: 11
caggtcgtgc agctggttgc                                               20

<210> SEQ ID NO 12
<211> LENGTH: 15
<212> TYPE: DNA
<213> ORGANISM: herpes simplex virus

<400> SEQUENCE: 12
ccttgatctc gtggc                                                    15
```